United States Patent
Li

(10) Patent No.: US 10,350,237 B2
(45) Date of Patent: Jul. 16, 2019

(54) CONDUCTIVE BIOMATERIAL FOR ENHANCEMENT OF CONDUCTION IN VITRO AND IN VIVO

(71) Applicant: University Health Network, Toronto (CA)

(72) Inventor: Ren-Ke Li, Toronto (CA)

(73) Assignee: University Health Network, Toronto, Ontario (CA)

( * ) Notice: Subject to any disclaimer, the term of this patent is extended or adjusted under 35 U.S.C. 154(b) by 0 days.

(21) Appl. No.: 14/765,992

(22) PCT Filed: Feb. 4, 2014

(86) PCT No.: PCT/CA2014/000091
§ 371 (c)(1),
(2) Date: Aug. 5, 2015

(87) PCT Pub. No.: WO2014/121378
PCT Pub. Date: Aug. 14, 2014

(65) Prior Publication Data
US 2015/0366900 A1  Dec. 24, 2015

Related U.S. Application Data

(60) Provisional application No. 61/760,858, filed on Feb. 5, 2013.

(51) Int. Cl.
*A61K 9/10* (2006.01)
*A61K 31/787* (2006.01)
(Continued)

(52) U.S. Cl.
CPC .......... *A61K 31/787* (2013.01); *A61K 31/785* (2013.01); *A61K 47/61* (2017.08);
(Continued)

(58) Field of Classification Search
None
See application file for complete search history.

(56) References Cited

U.S. PATENT DOCUMENTS

2006/0233850 A1* 10/2006 Michal .................... A61L 27/20
424/422
2008/0242738 A1   10/2008 Marks et al.
(Continued)

OTHER PUBLICATIONS

Ismail et al., Sensors and Actuators B, 2011, 160(1), pp. 1180-1190.*
(Continued)

*Primary Examiner* — Brian Gulledge
(74) *Attorney, Agent, or Firm* — Norton Rose Fulbright Canada LLP; Jung-Kay Chiu

(57) ABSTRACT

A biocompatible, electrically conductive biomaterial capable of earn carrying the electrical potential of a cardiac impulse and comprising (1) a conductive polymer such as polyaniline, polypyrrole or polythiophene, and (ii) a biocompatible component such as a polysaccharide, a protein, or a polypeptide, in particular chitosan or gelatin, is described. The material can take the form of a hydrogel, membrane, sheet or mesh. It can be used to restore or improve electrical impulse propagation across damaged tissue or scar region of the myocardium, in particular in the ti treatment of myocardial infarction and arrhythmia.

8 Claims, 25 Drawing Sheets

Synthesis of Ch-PPy

PPy-Chitosan Graft or

Chitosan chemical structure

Conducting Graft

ᴡᴡ - Chitosan

ʃ - Poly(pyrrole), PPy

• - Primary amine group

(51) Int. Cl.
| | |
|---|---|
| A61K 31/785 | (2006.01) |
| A61L 27/26 | (2006.01) |
| A61L 27/50 | (2006.01) |
| A61L 31/04 | (2006.01) |
| A61L 31/14 | (2006.01) |
| C08G 61/12 | (2006.01) |
| A61K 47/61 | (2017.01) |
| A61K 47/64 | (2017.01) |
| A61K 47/69 | (2017.01) |
| A61K 9/00 | (2006.01) |
| A61K 47/36 | (2006.01) |

(52) U.S. Cl.
CPC ...... *A61K 47/6435* (2017.08); *A61K 47/6903* (2017.08); *A61L 27/26* (2013.01); *A61L 27/50* (2013.01); *A61L 31/041* (2013.01); *A61L 31/14* (2013.01); *C08G 61/124* (2013.01); *A61K 9/0024* (2013.01); *A61K 47/36* (2013.01); *A61L 2400/06* (2013.01); *A61L 2430/20* (2013.01); *C08G 2261/128* (2013.01); *C08G 2261/3221* (2013.01)

(56) References Cited

U.S. PATENT DOCUMENTS

2009/0123412 A1* 5/2009 Healy ............... A61K 9/0019
424/78.17
2012/0100217 A1* 4/2012 Green ............... H01B 1/122
424/487

OTHER PUBLICATIONS

Chen, Y. et al., "Synthesis and Properties of Polypyrrole/Chitosan Composite Hydrogels," Journal of Macromolecular Science, Part A: Pure and Applied Chemistry, vol. 50, No. 12, pp. 1225-1229, 2013.

Guarino, V. et al., "Conductive PANi/PEGDA Macroporous Hydrogels For Nerve Regeneration," Adavanced Healthcare Materials, vol. 2, No. 1, pp. 218-227, 2013.

Hsiao, C-W. et al., "Electrical coupling of isolated cardiomyocyte clusters grown on aligned conductive nanofibrous meshes for their synchronized beating," Biomaterials, vol. 34, No. 4, pp. 1063-1072, 2013.

International Search Report and Written Opinion for PCT/CA2014/000091 dated Apr. 29, 2014.

Ismail, Y. A. et al., "Sensing characteristics of a conducting polymer/hydrogel hybrid microfiber artificial muscle," Sensors and Actuators B: Chemical, vol. 160, No. 1, pp. 1180-1190, 2011.

Kai, D. et al., "Polypyrrole-contained electrospun conductive nanofibrous membranes for cardiac tissue engineering," vol. 99A, No. 3, pp. 376-385, 2011.

Mobarakeh-Ghasemi, L. et al., "Application of conductive polymers, scaffolds and electrical stimulation for nerve tissue engineering," J. Tissue Engineering and Regenerative Medicine, vol. 5, No. 4, pp. e17-e35, 2011.

Edson G. R. Fernandes et al: "Electrospinning of Hyperbranched Poly-L-Lysine/polyaniline Nanofibers for Application in Cardiac Tissue Engineering" Journal of Macromolecular science, Part A—Pure and Applied Chemistry., vol. 47, No. 12, Oct. 18, 2010 p. 1203-1207, XP055293960, US ISSN: 1060-1325.

European Search Report for 14748519.7 dated Aug. 12, 2016, p. 1-7.

Li M Et al: "Electrospinning polyaniline-contained gelatin nanofibers for tissue engineering applications", Biomaterials, Elsevier science publishers BV., Barking, GB, vol. 27, No. 13, May 1, 2006 p. 2705-2715, XP027951057, ISSN: 0142-9612.

Thanpitcha T et al: "Preparation and characterization of polyaniline/chitosan blend film" Carbohydrare Polymers, Applied Science Publishers, Ltd. Barking, GB, vol. 64, No. 4, Jun. 16, 2006 p. 560-568, XP027941481, ISSN: 0144-8617.

\* cited by examiner

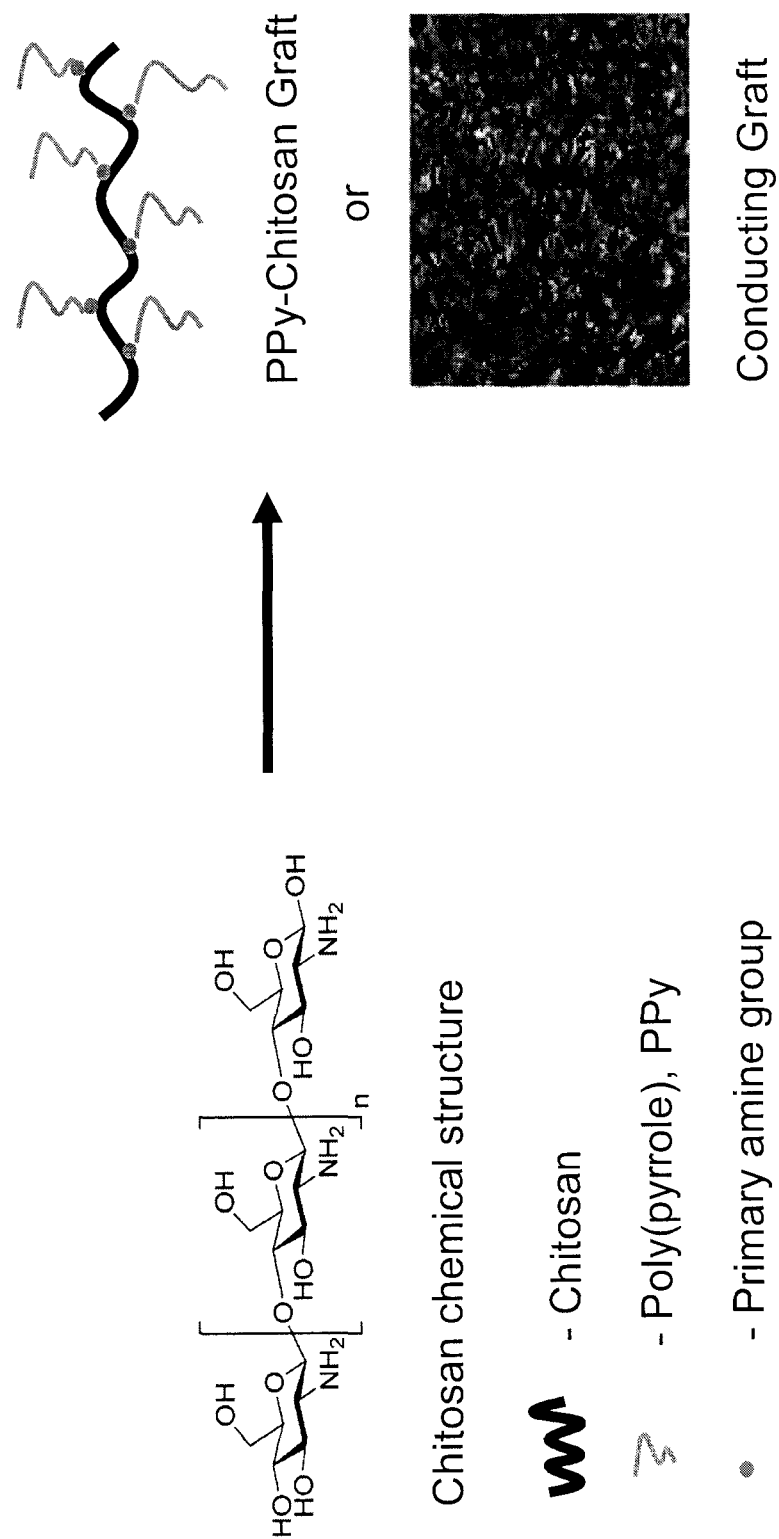
Figure 1: Synthesis of Ch-PPy

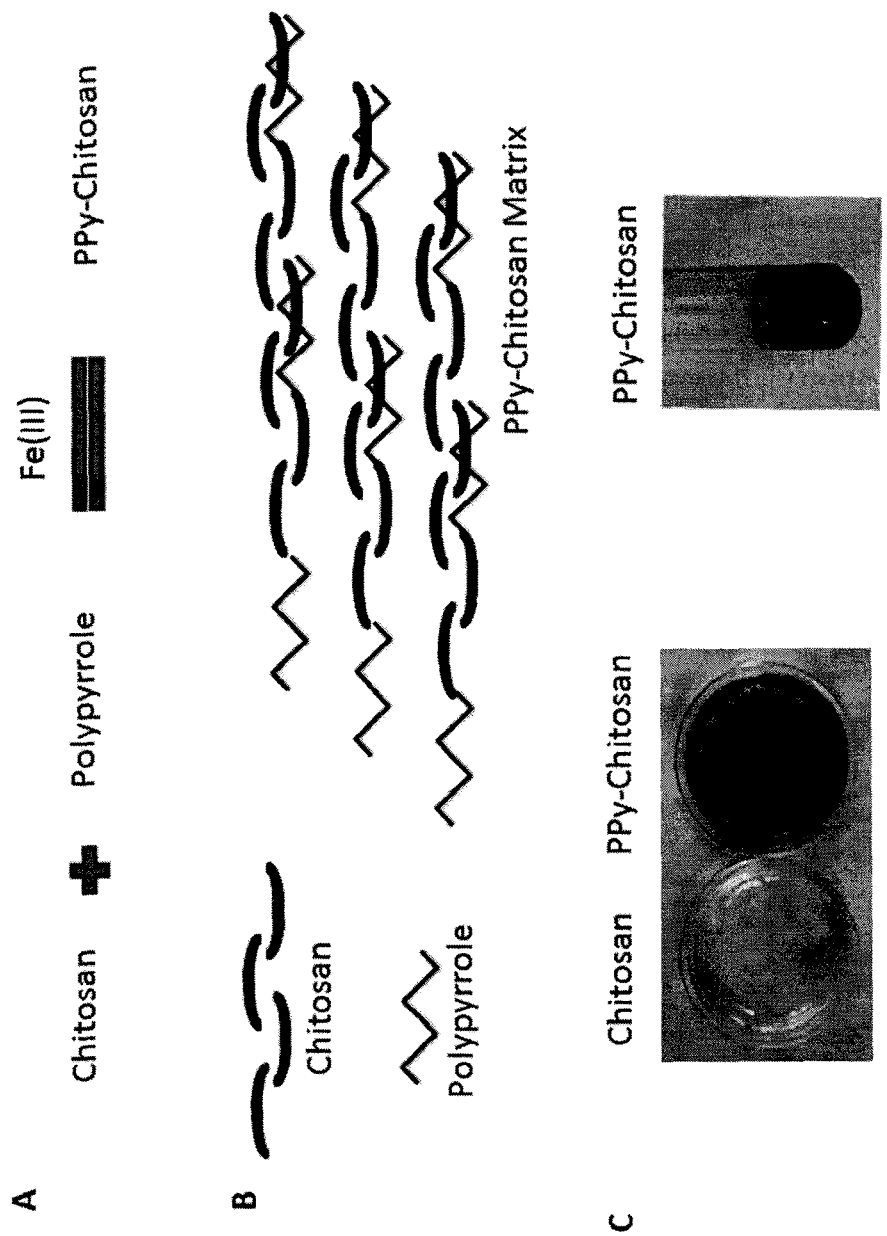
Figure 2: Synthesis of Polypyrrole Chitosan

Figure 3: Ch-PPy gelation time.

| | Gluteraldehyde(µL/mL Ch-PPy) | Gelation time (minutes) |
|---|---|---|
| FeCl3-Ch | 1.25 | 1 |
| 2.84 PPy-Ch | 1.5 | 1 |
| 28.4 PPy-Ch | 1.5 | 1 |
| 284 PPy-Ch | 2.5 | 1 |

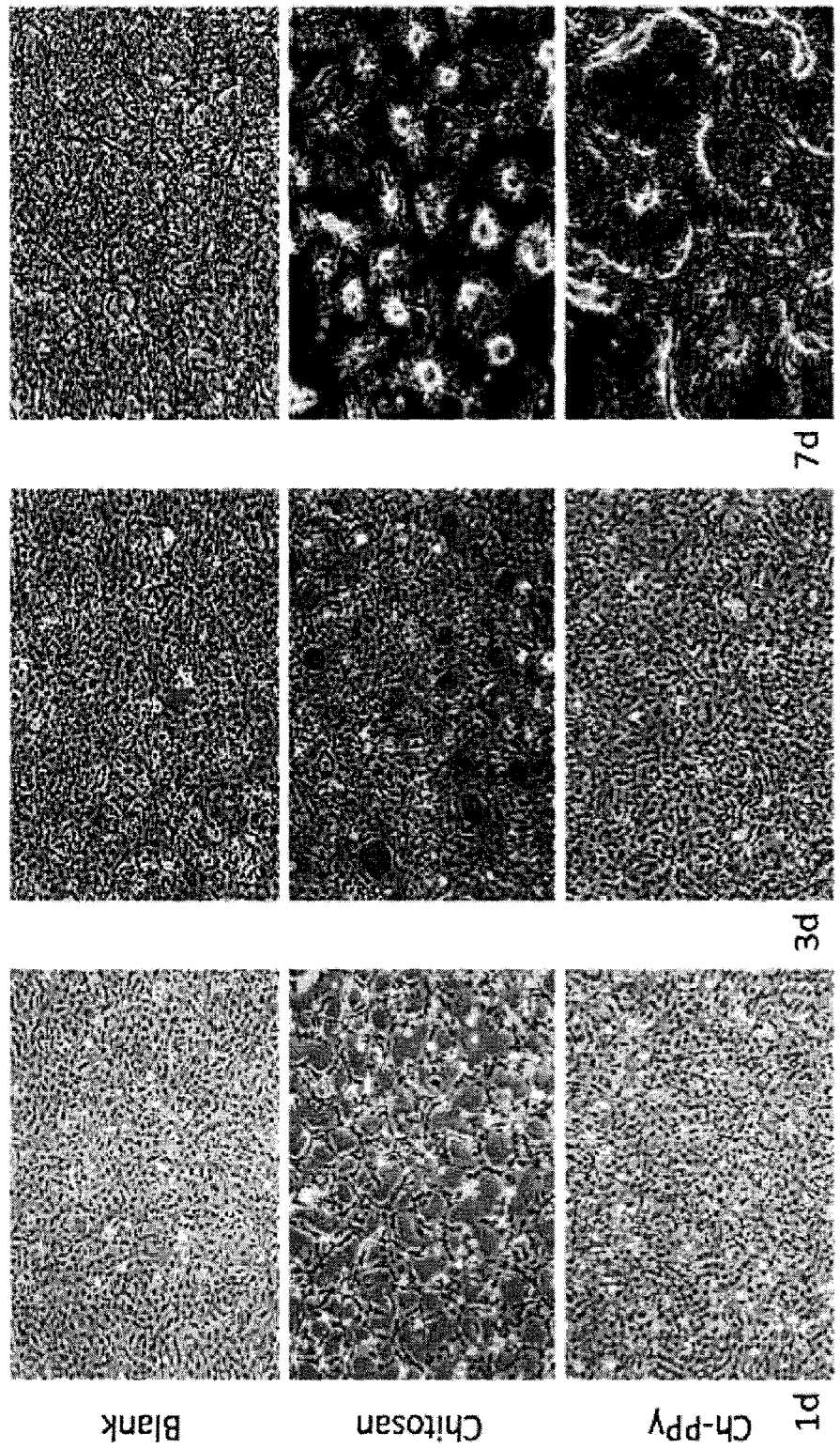

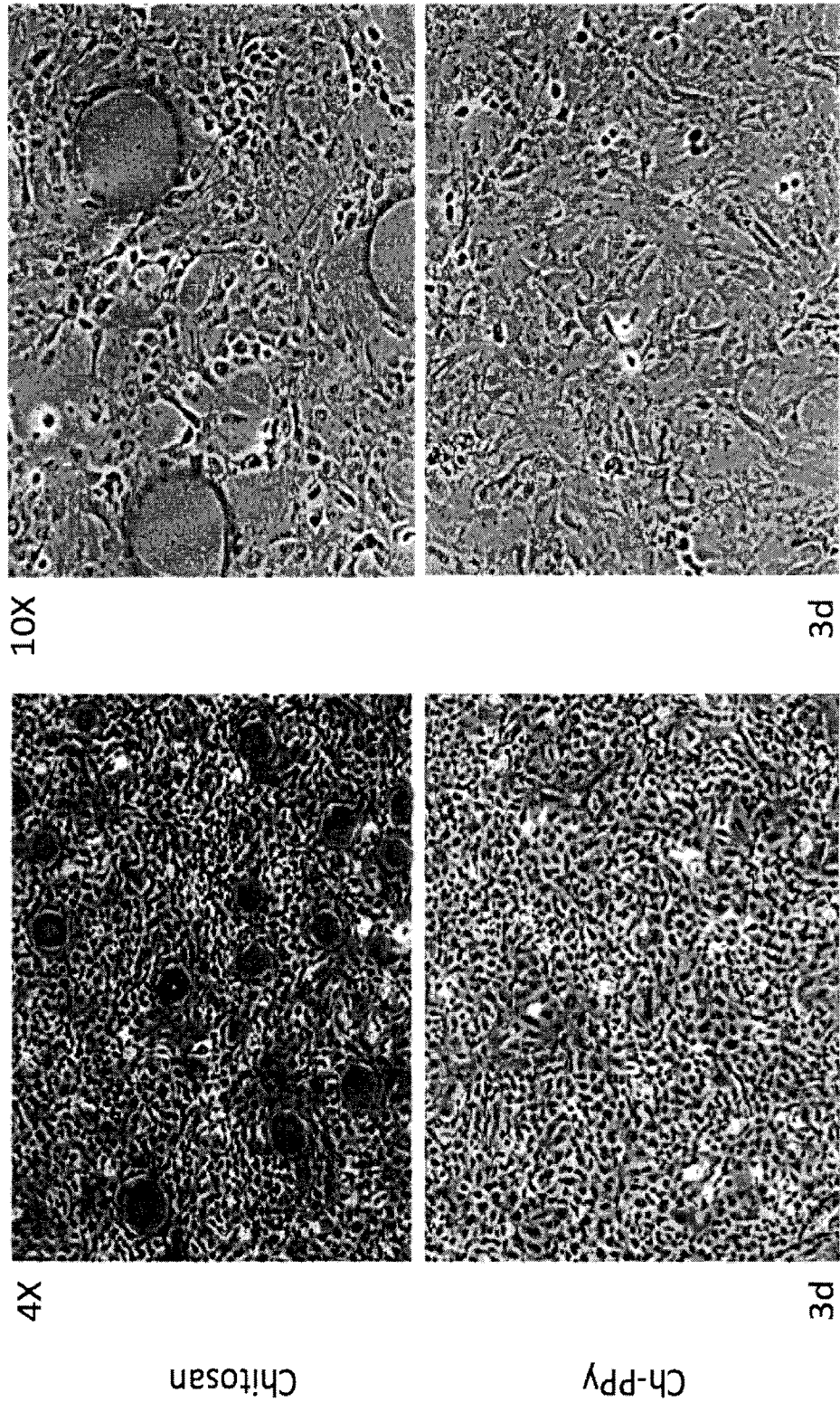
Figure 5: Smooth Muscle Cell Attachment on biomaterials.

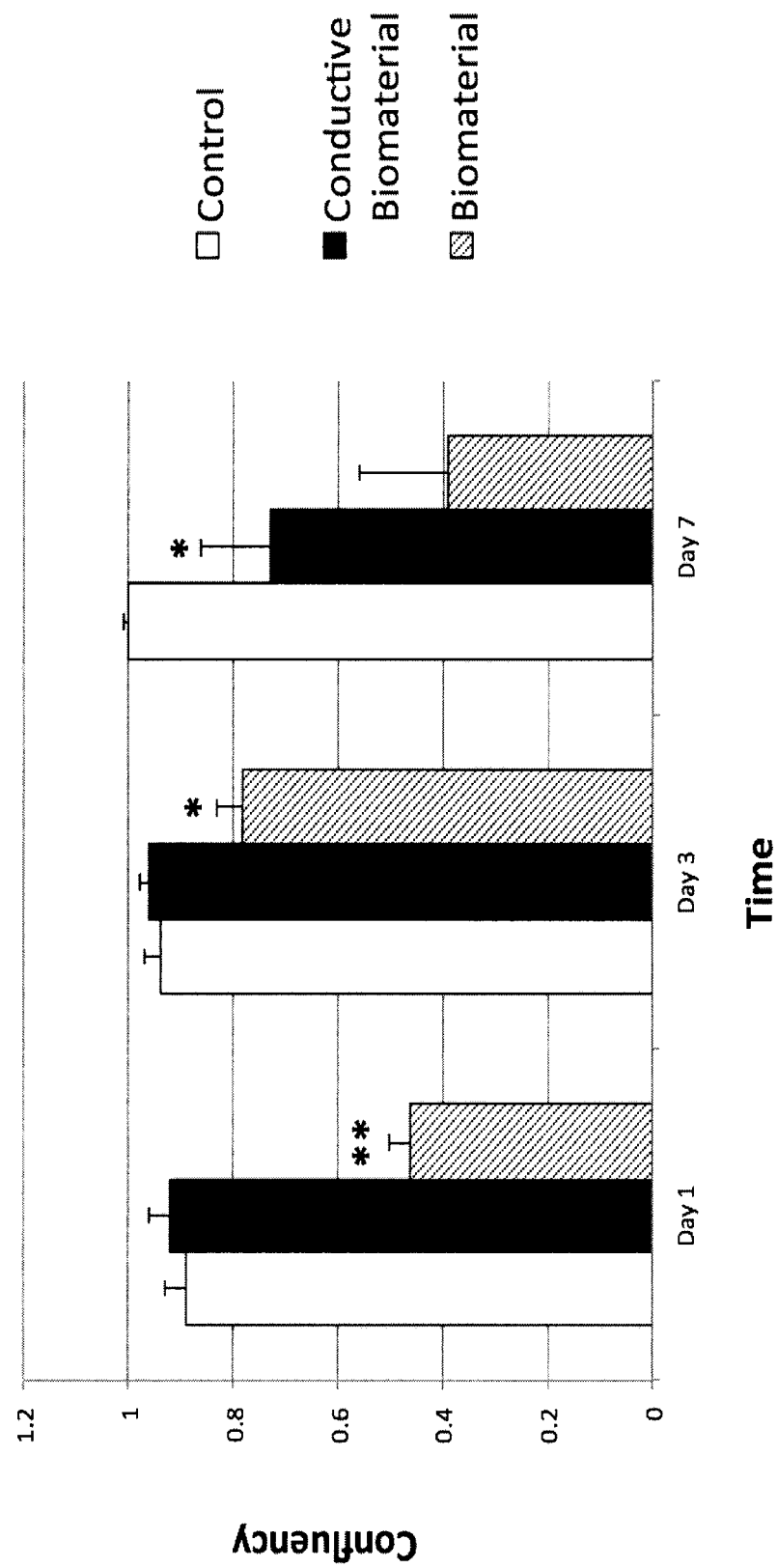
Figure 6: Smooth Muscle Cell Attachment

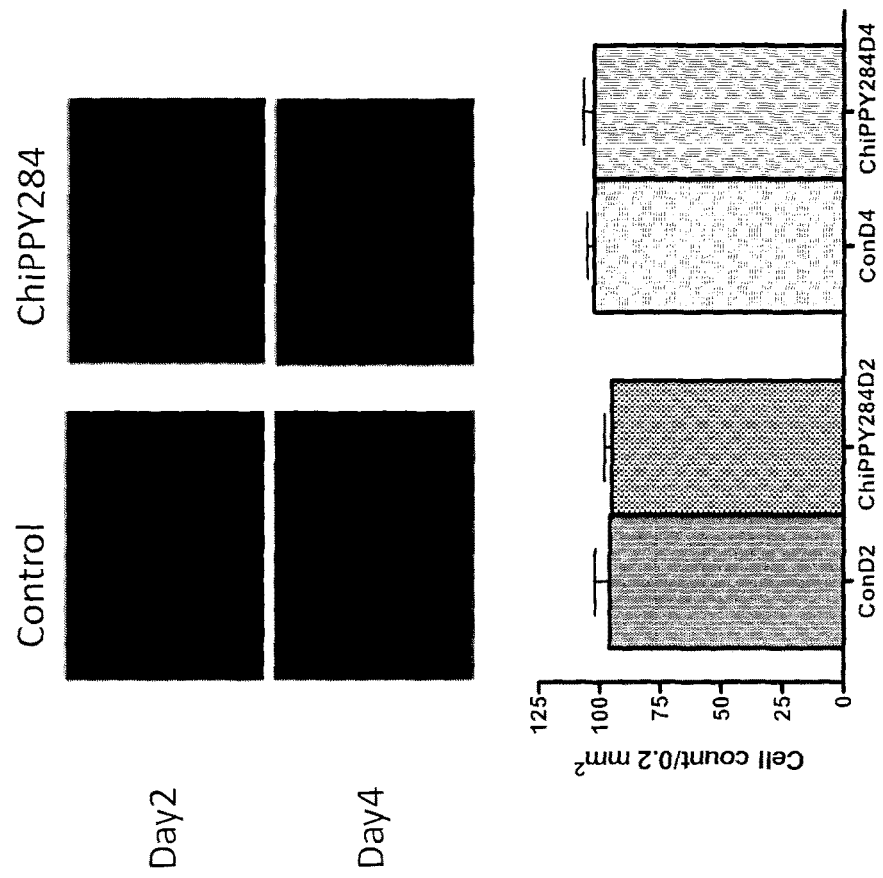
Figure 7: Smooth Muscle Cell Proliferation using DAPI Staining Imaged at 2, 4 days.

Figure 8: Ch-PPy and Chitosan injection size at Day 0.

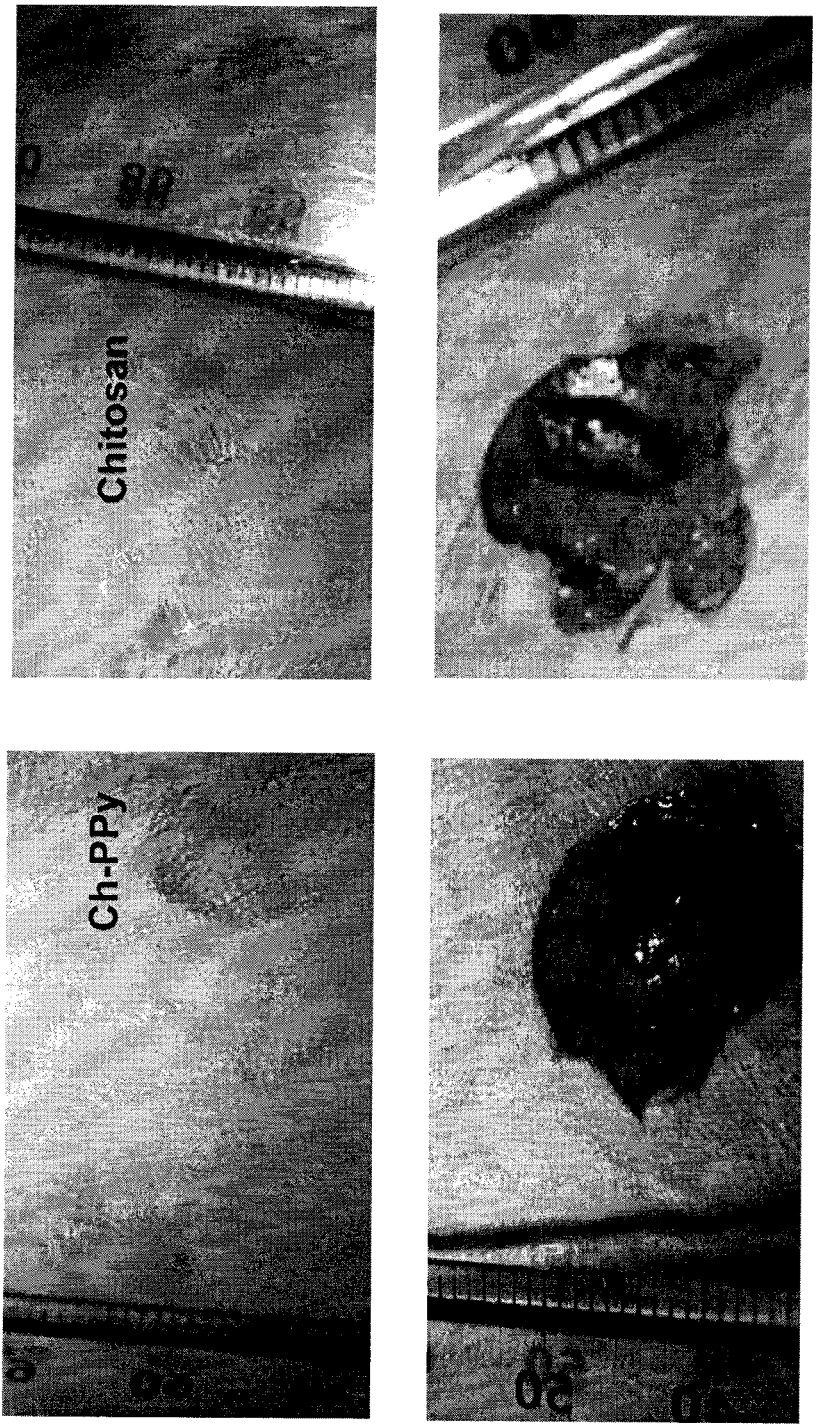
Figure 9: 12 weeks after Ch-PPy and Chitosan injection.

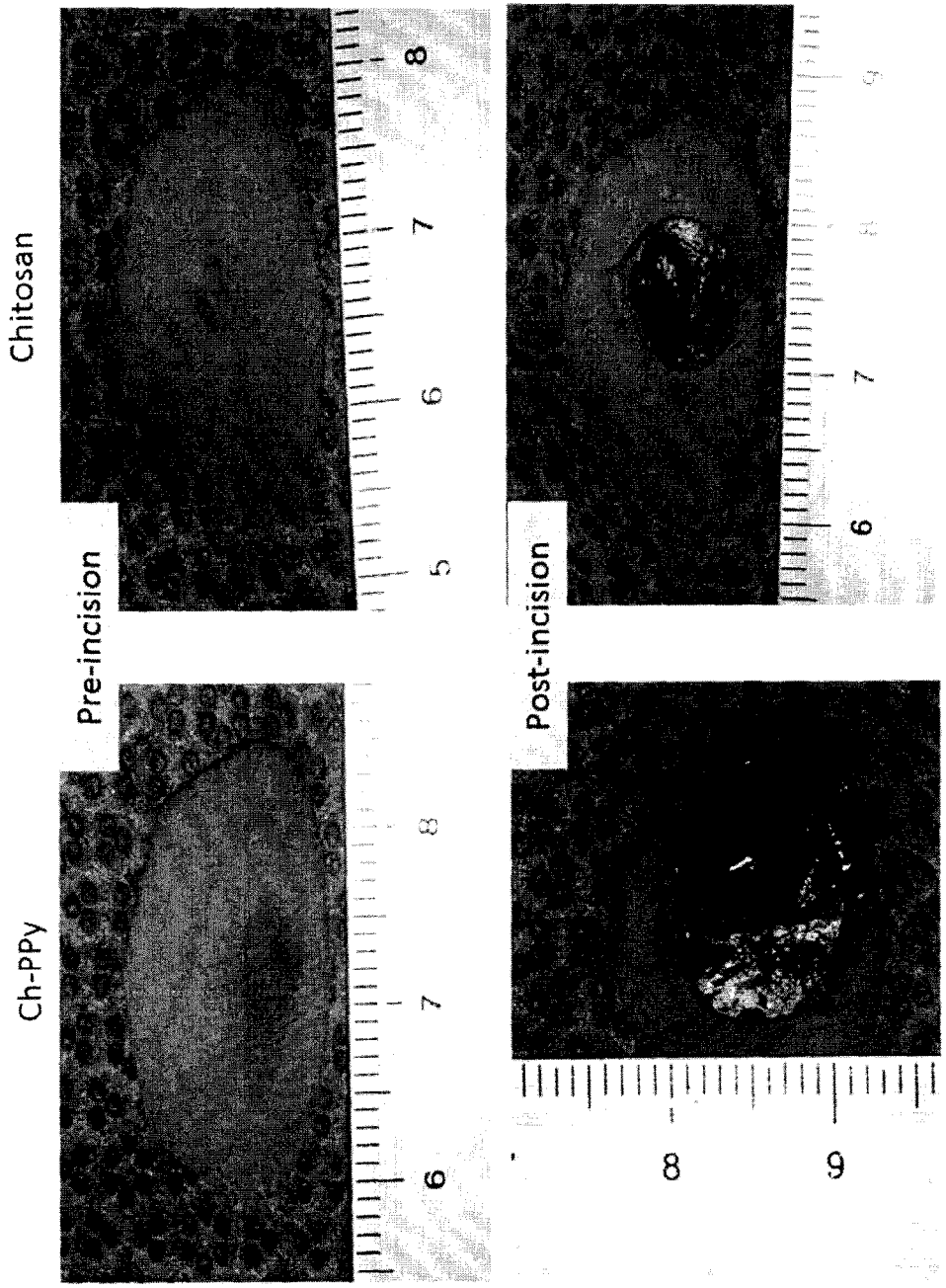

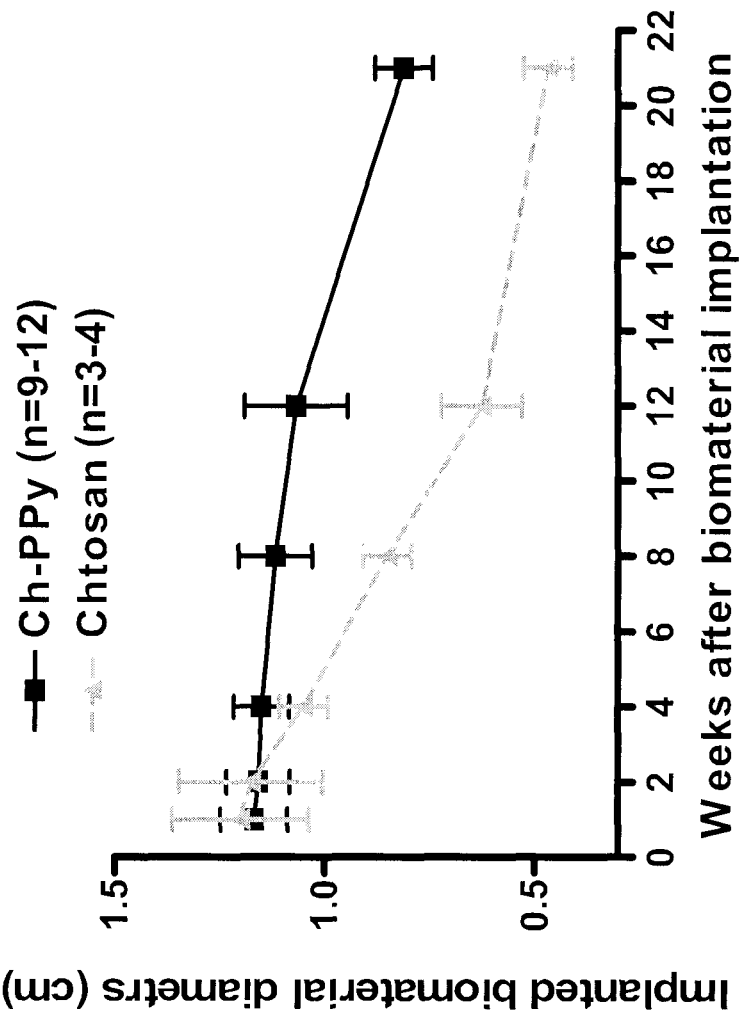
Figure 11: Biodegradation of Ch-PPy and Chitosan.

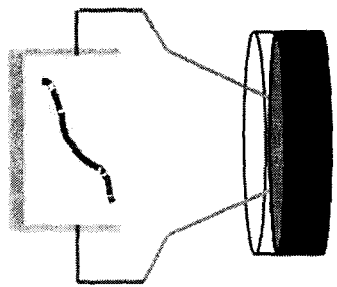
Figure 12: Experimental Setup of 2-point probe for conductivity measurements

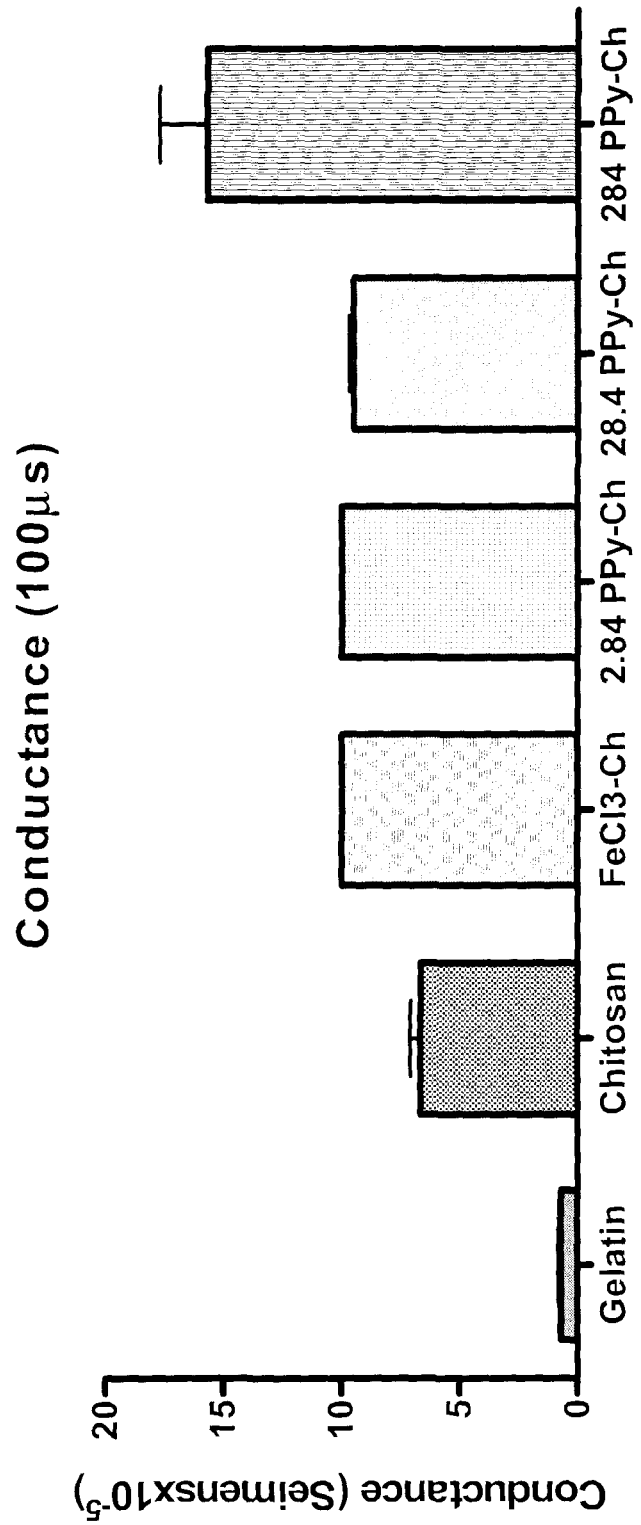
Figure 13: Conductance Measurements

Figure 14: Custom-fabricated cuvette and voltammograms
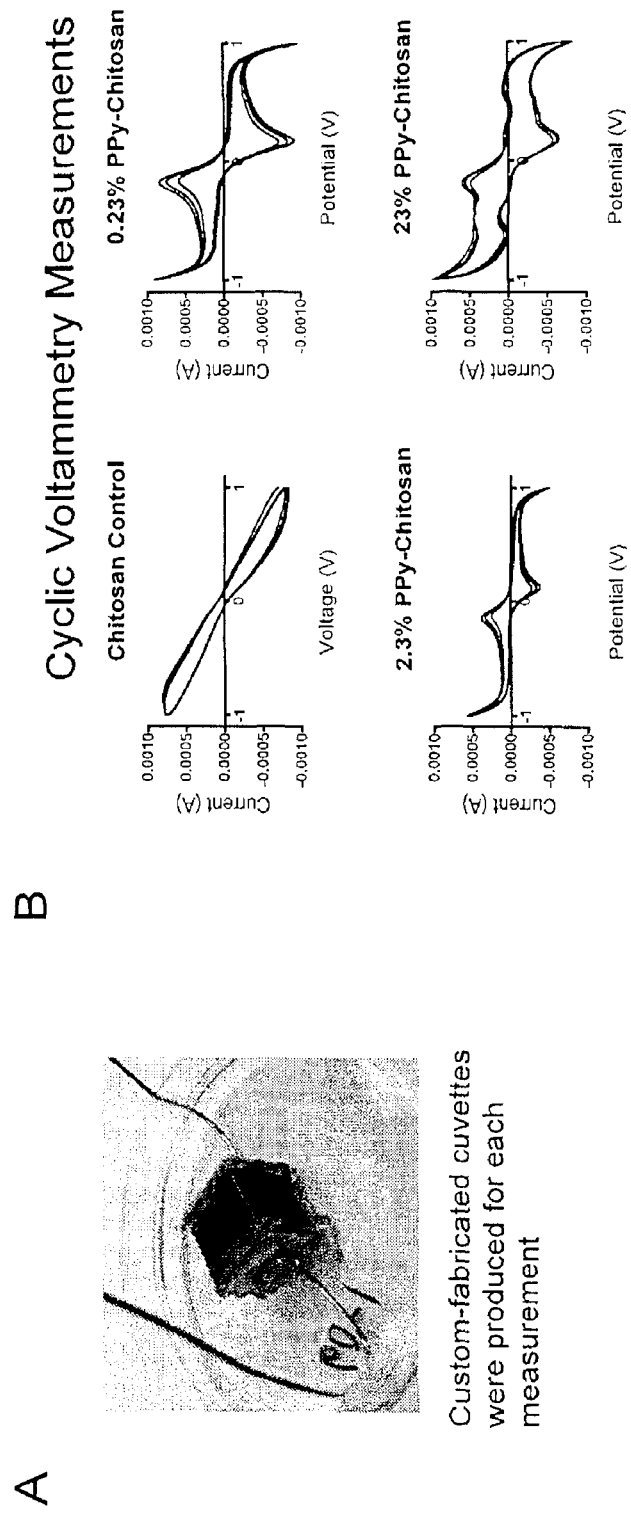

Figure 15: EIS measurements
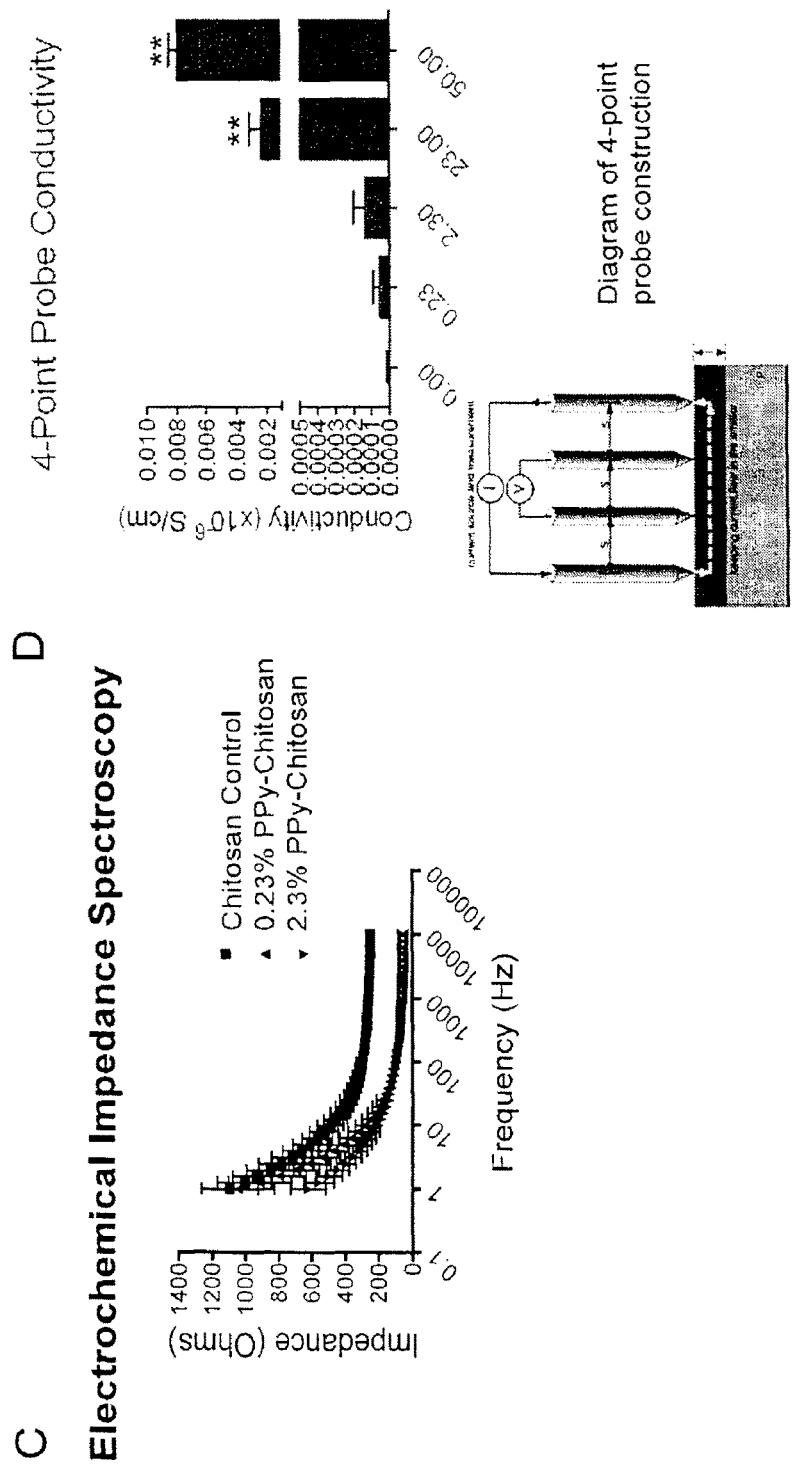

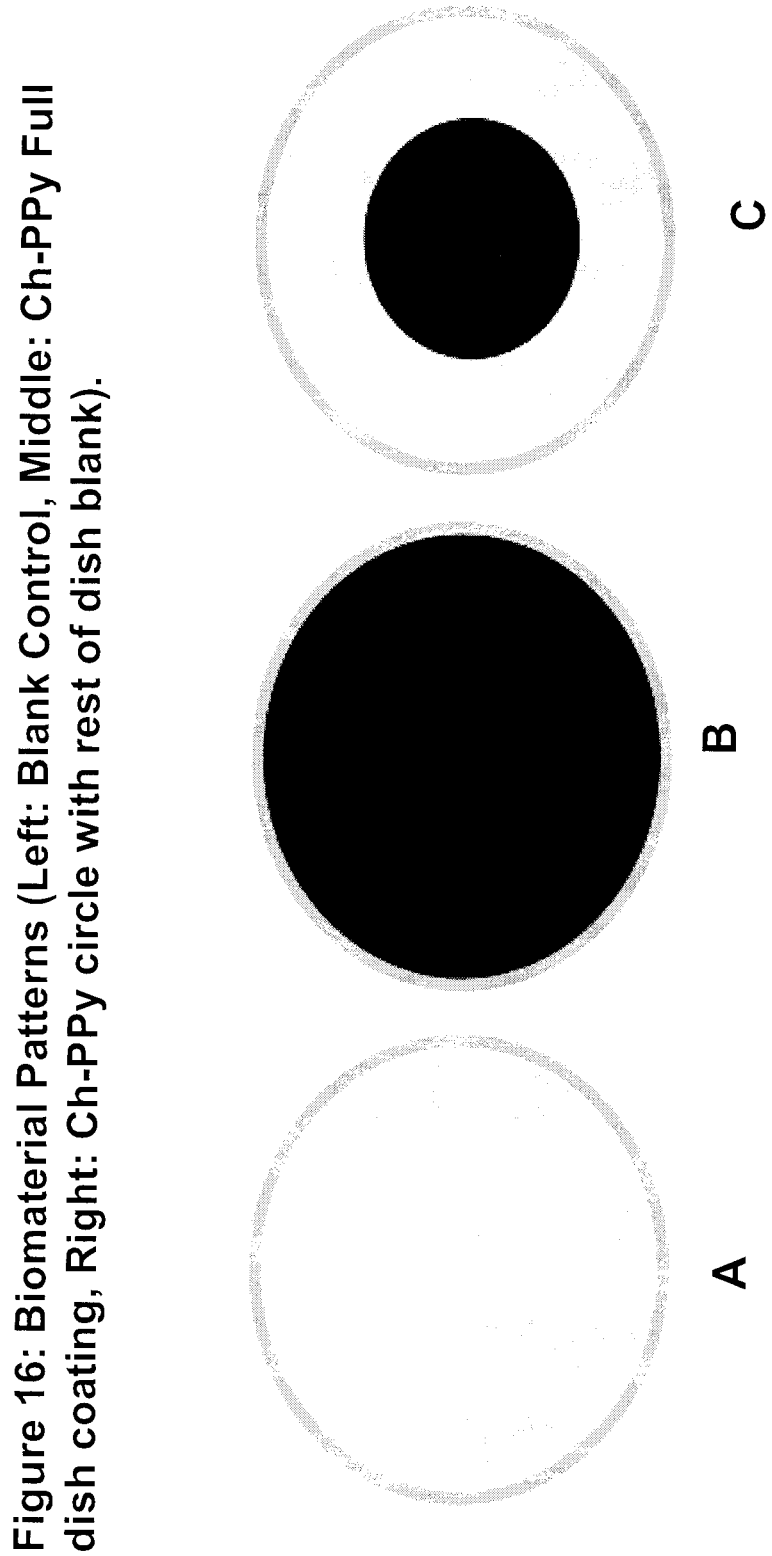
Figure 16: Biomaterial Patterns (Left: Blank Control, Middle: Ch-PPy Full dish coating, Right: Ch-PPy circle with rest of dish blank).

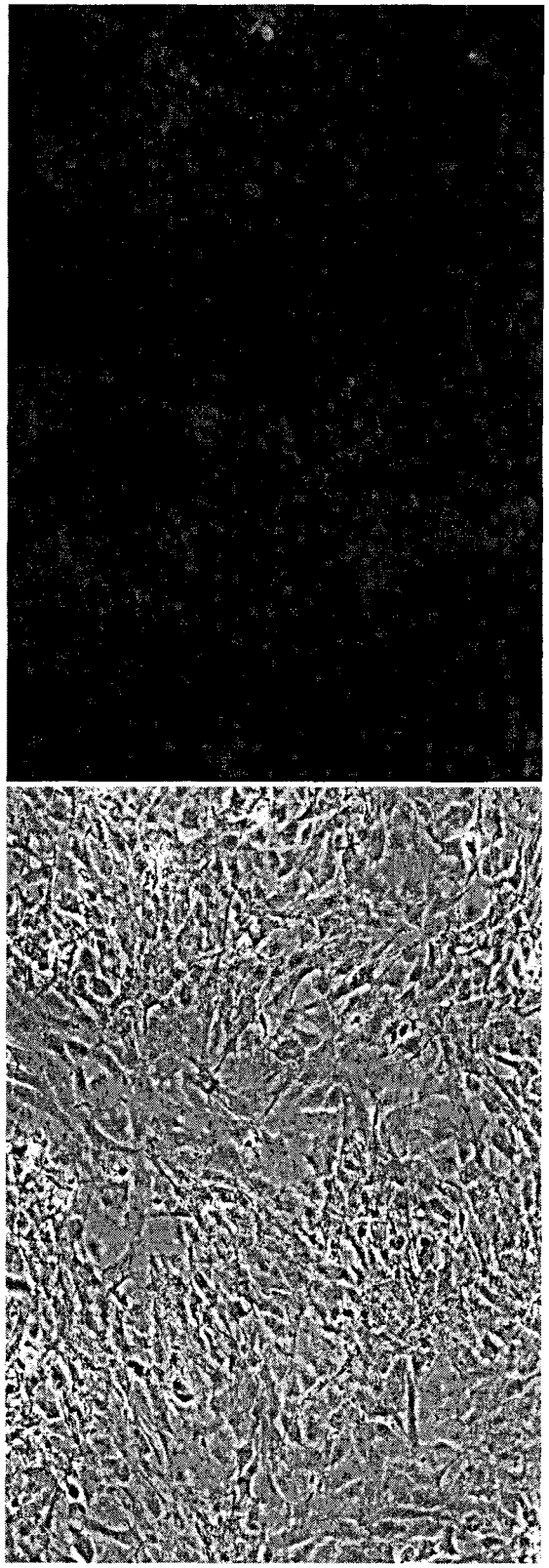
Figure 17: Neonatal cardiomyocyte in culture dish (left panel) and stained for DAPI (right panel).

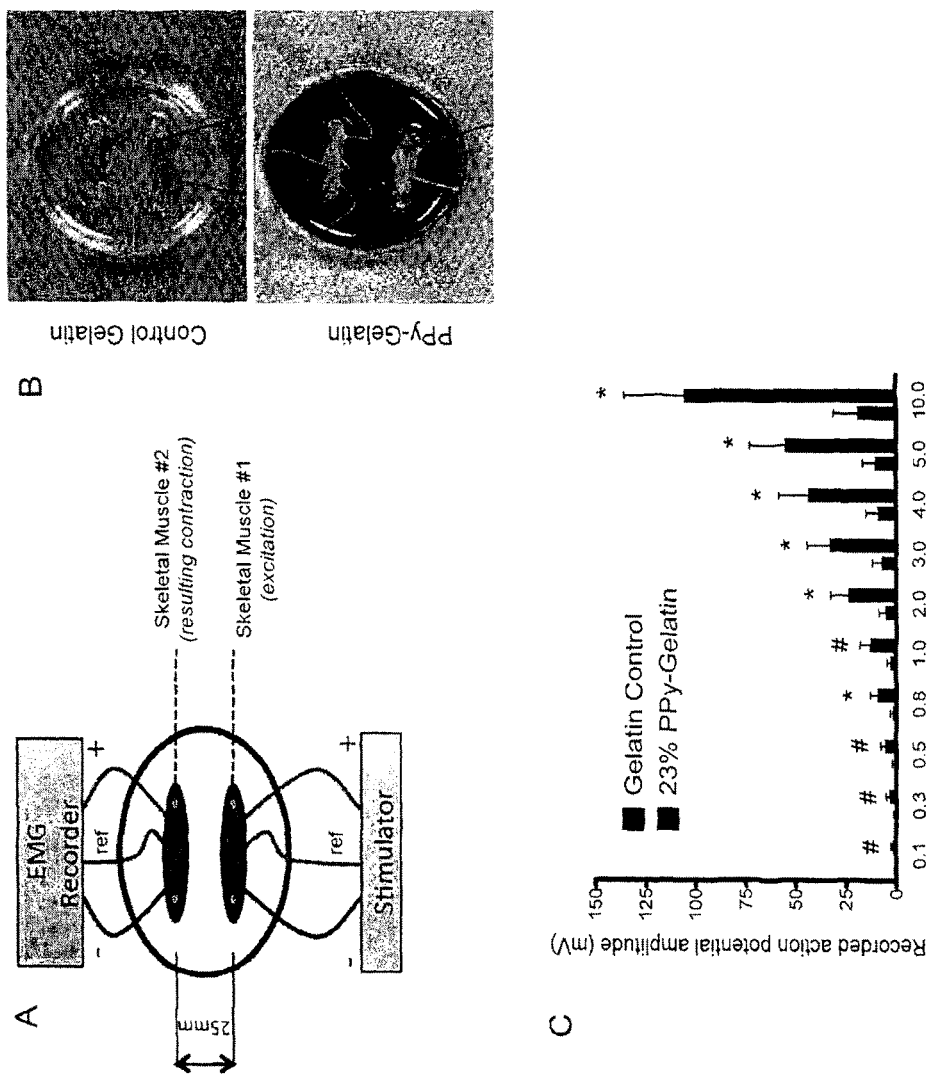
Figure 18: Two Muscle Experiment Results

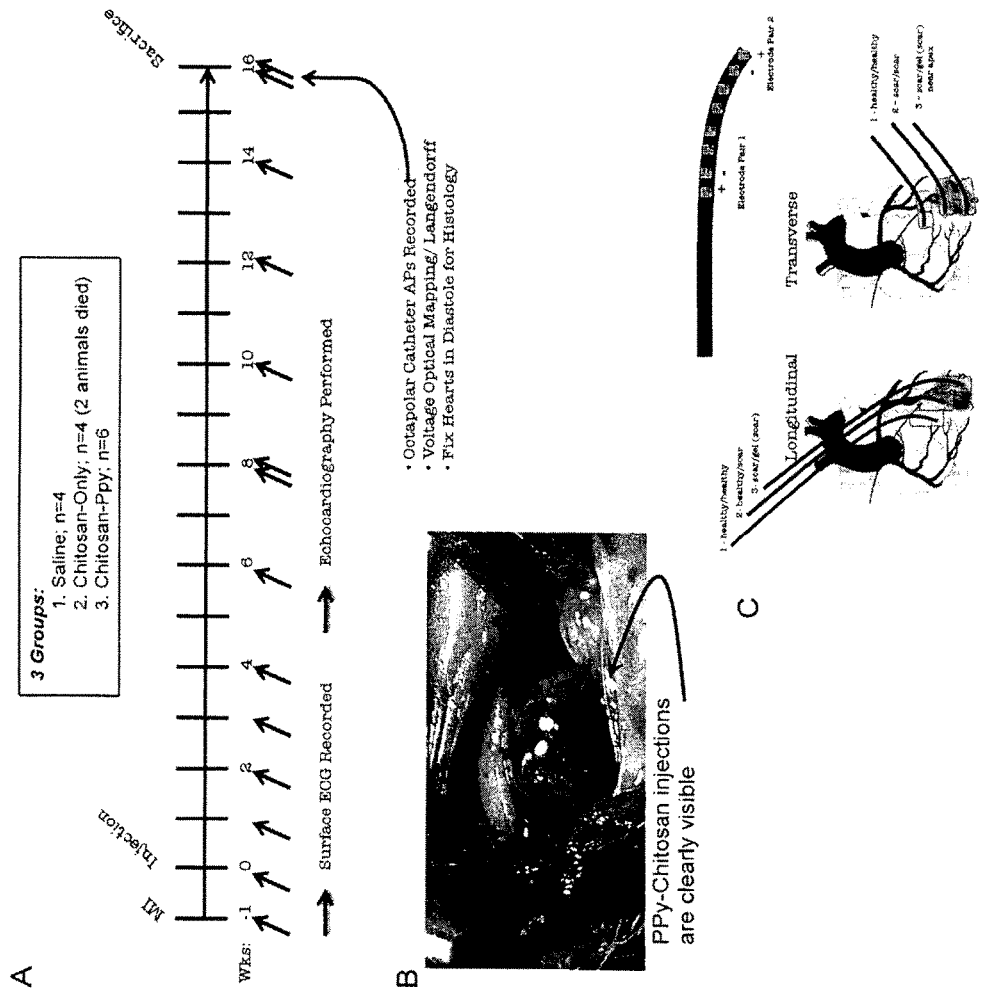
Figure 19: Assessment via *in vivo* model

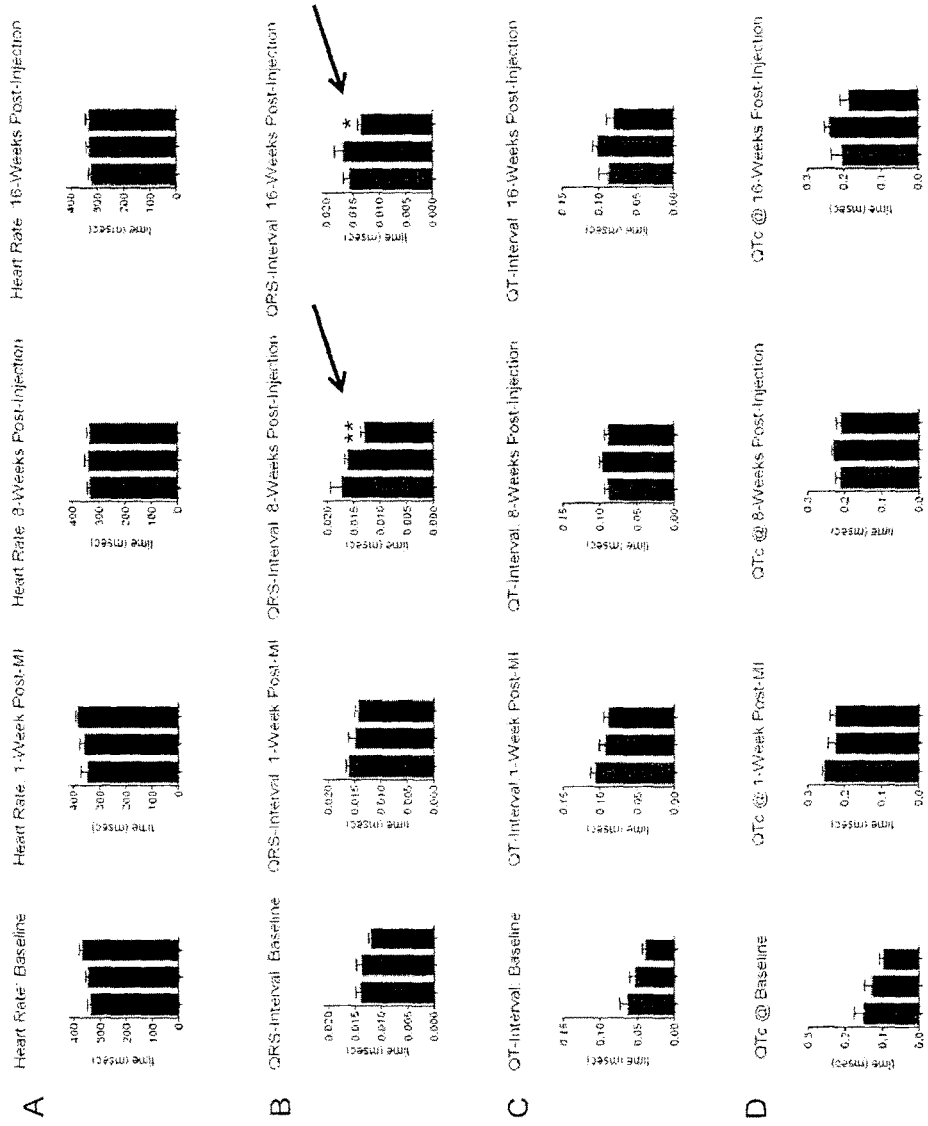
Figure 20: Surface ECGs from *in vivo* Study
Legend: First Column is Saline, Second Col. is chitosan control, Third Col. is PPy-Ch

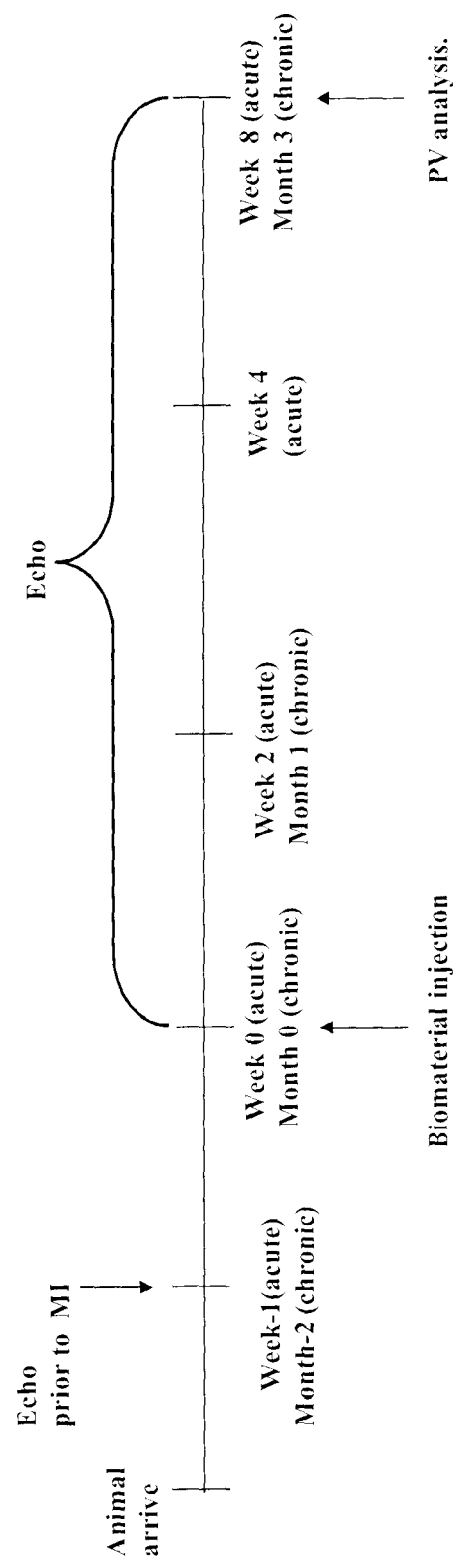
Figure 21: Schematic timelines of *in vivo* animal study.

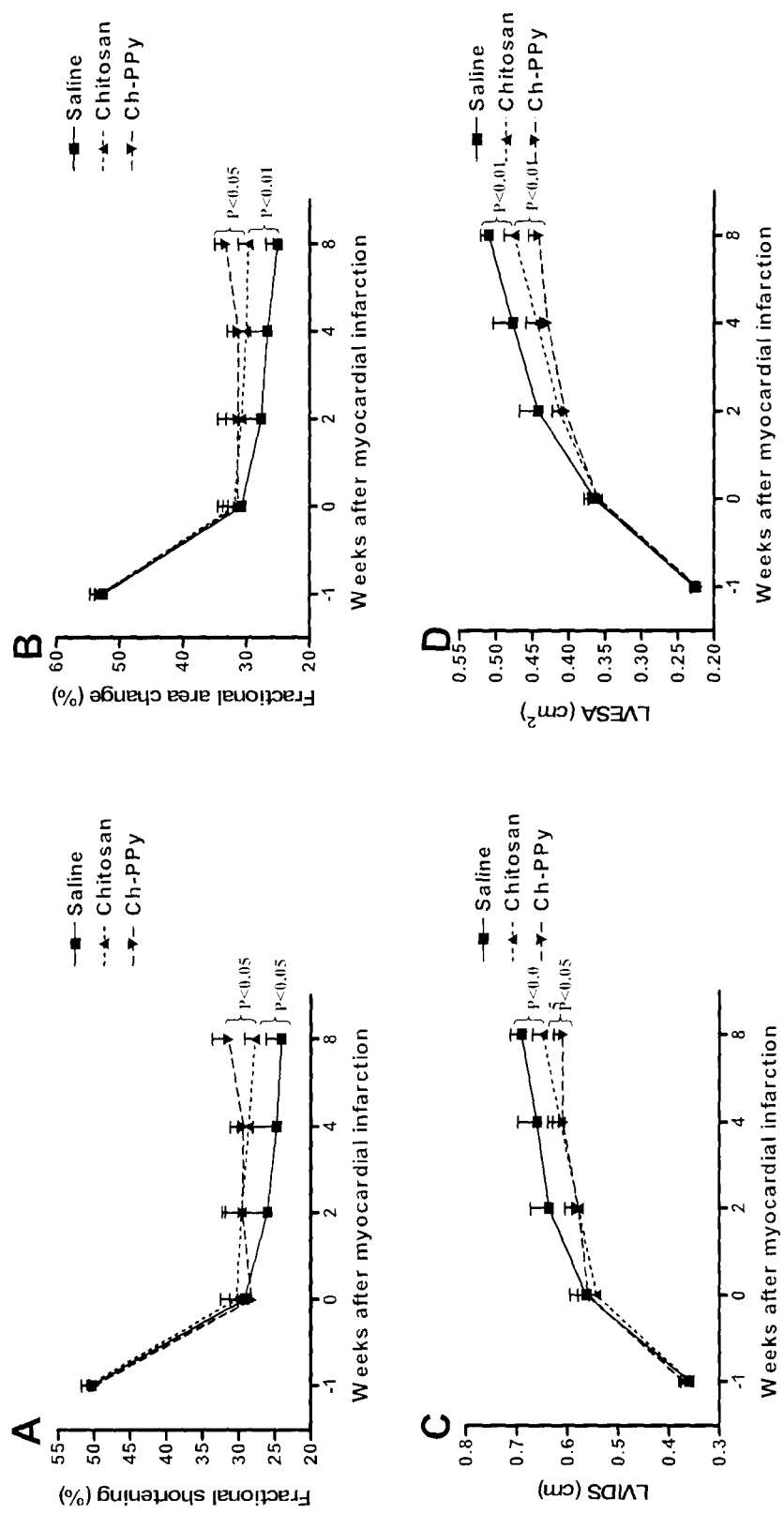
Figure 22: Cardiac function by echocardiography.

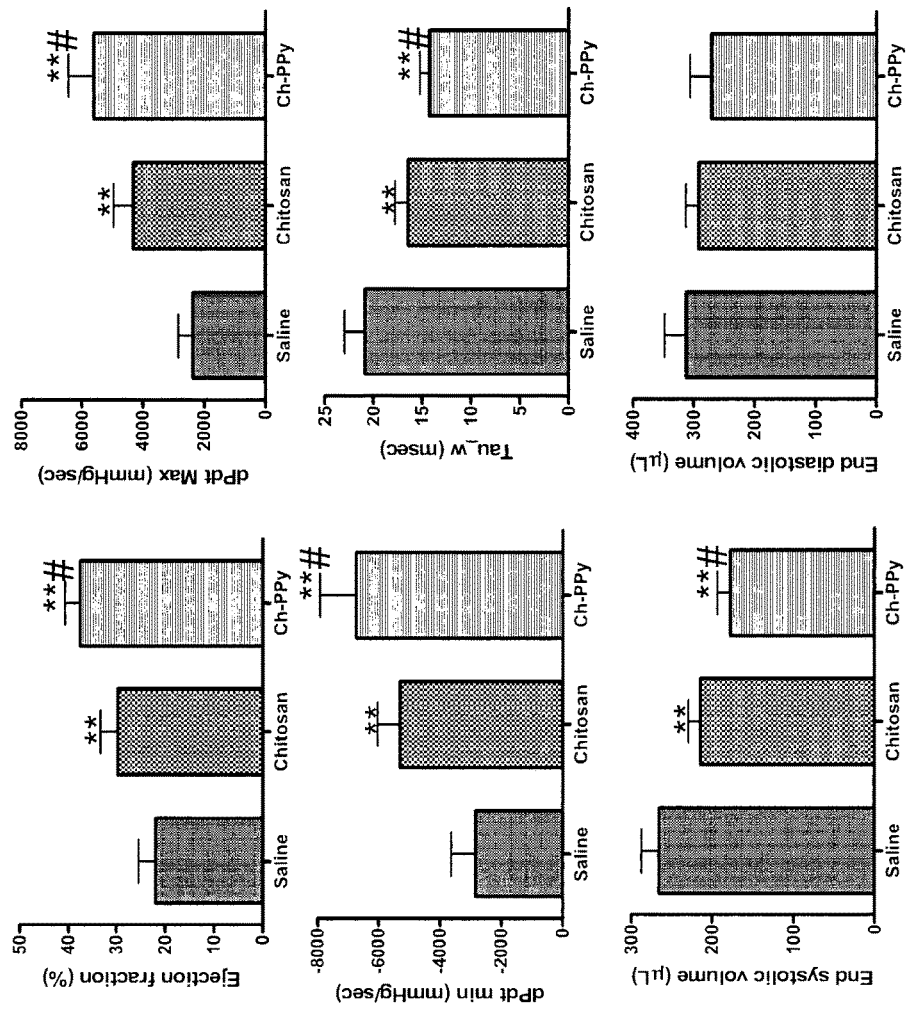
Figure 23: Load-dependent cardiac function and LV volumes by pressure-volume (P-V) catheter.

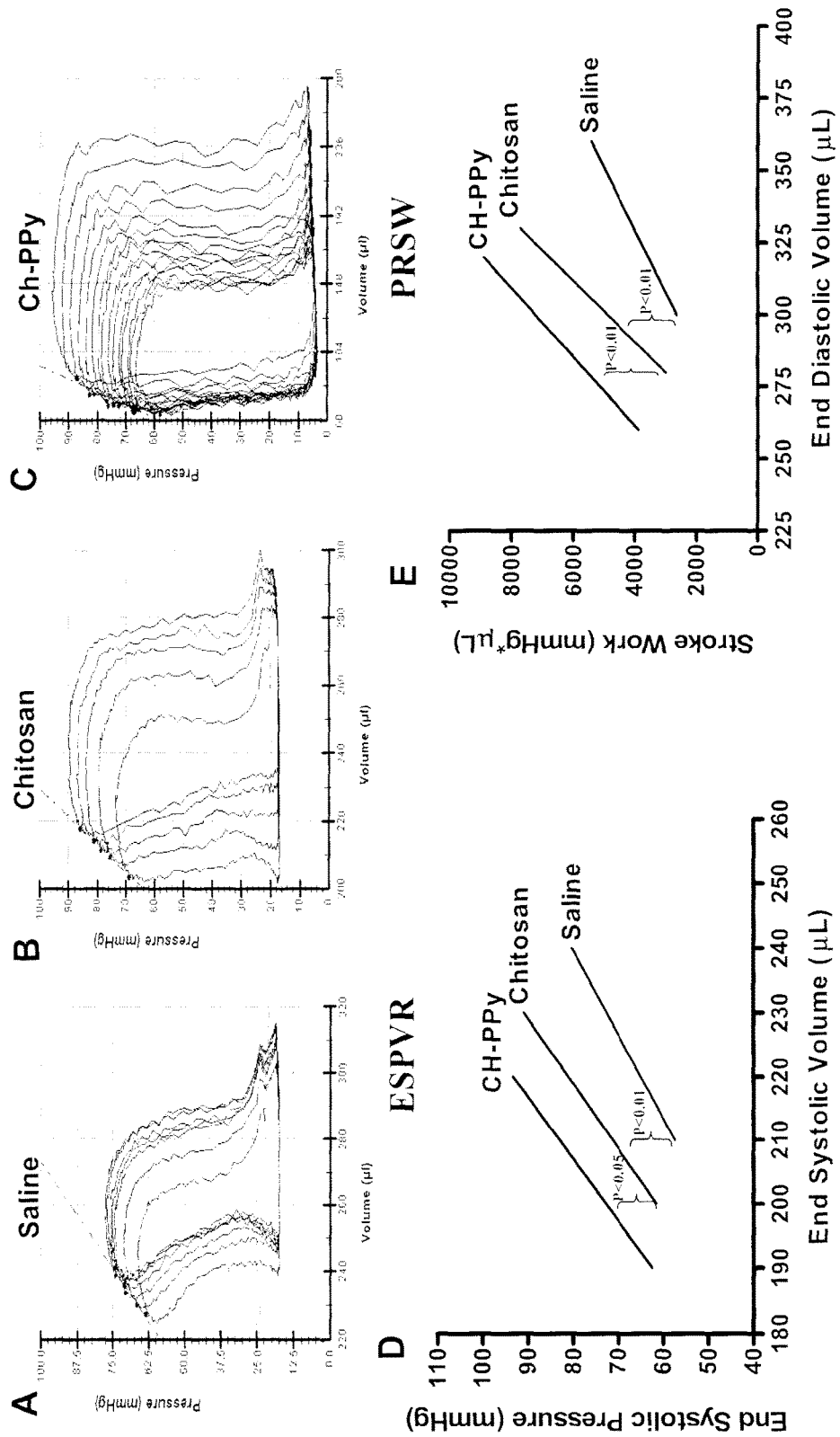
Figure 24: Load-independent cardiac function by P-V catheter.

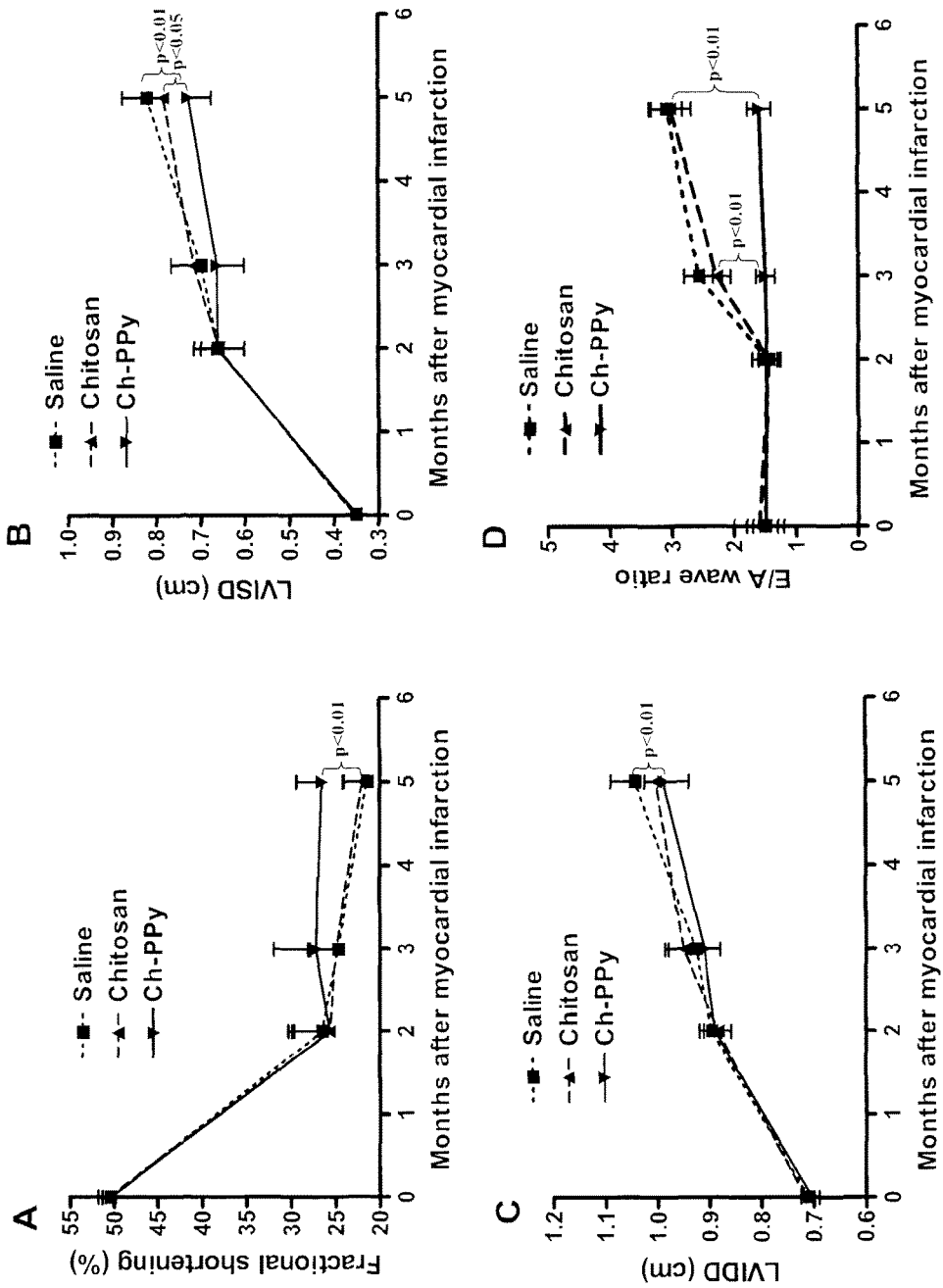
Figure 25: Cardiac function by echocardiography.

CONDUCTIVE BIOMATERIAL FOR ENHANCEMENT OF CONDUCTION IN VITRO AND IN VIVO

CROSS-REFERENCE TO RELATED APPLICATIONS

This application is a 35 U.S.C. § 371 national stage filing of International Application No. PCT/CA2014/000091, filed Feb. 4, 2014, which claims priority to U.S. provisional patent application No. 61/760,858, filed Feb. 5, 2013, the entire contents of each of which is incorporated herein by reference.

FIELD OF THE TECHNOLOGY

The present disclosure relates to a biocompatible, electrically conductive biomaterial capable of carrying the electrical potential of a cardiac impulse. The present disclosure also relates to treatments using the electrically conductive biomaterial.

BACKGROUND

Treatments of heart conditions, such as myocardial infarction (MI), mainly include medication, medical interventional therapy and surgery, such as coronary artery bypass graft surgery. These treatments can unclog the occlusive blood vessels and improve the symptom of myocardial ischemia. They cannot, however, enhanced cardiac conduction or have limited improvement of cardiac function.

Following a myocardial infarction, a non-contractile fibrotic scar forms. Scar formation can be associated with widespread cardiomyocyte death and impaired electrical properties, such as slowing of electrical impulse propagation across the scar region of the myocardium. In addition, "passive" barriers can develop that produce unidirectional block or delay in atrioventricular (AV) electrical conduction, or even produce deadly reentrant arrhythmias. Currently, there are few direct treatments of these underlying conditions.

The present disclosure relates to a biocompatible, electrically conductive material capable of treating heart conditions including myocardial infarction and other related conditions. For example, the electrically conductive biomaterial can restore or improve electrical impulse propagation across the damaged tissue or scar region of the myocardium and resolve "passive" barriers to atrioventricular electrical conduction.

SUMMARY

The present disclosure relates to a modified biomaterial that can be adapted to deliver an electrically conductive adjuvant (e.g., conductive polymer) to the heart. The modified biomaterial can be used to treat heart related conditions, such as MI and arrhythmia.

In one embodiment, the present disclosure relates to a biocompatible material comprising a conductive polymer and a biocompatible component. The conductive polymer can include polypyrrole-based polymers, such as polypyrrole. The biocompatible component can include a polysaccharide, protein or polypeptide, such as chitosan or gelatin. The conductive biocompatible material can be incorporated into, or made into, a conductive hydrogel, membrane, sheet, graft, or mesh.

In another embodiment, the present disclosure relates to a method of treating a heart condition, the method comprising introducing a biocompatible material to the heart, wherein the material includes a conductive polymer and a biocompatible component. The heart condition can include myocardial infarction, heart failure, atrioventricular block, arrhythmia and a conduction abnormality. The disclosure also relates to use of a biocompatible material for treating a heart condition in an individual, wherein the material includes a conductive polymer and a biocompatible component.

BRIEF DESCRIPTION OF THE DRAWINGS

FIG. 1 shows the synthesis of PPy-chitosan grafts.

FIG. 2 shows the synthesis of a PPy-chitosan matrix or hydrogel, with the chemical conjugation with polypyrrole side chains.

FIG. 3 shows the results of a gelation test using gluteraldehyde as the crosslinker.

FIG. 4 shows SEM images of SMCs taken using low magnification. The SMCs were cultured for 1, 3, and 7 days, and then imaged using bright field microscopy.

FIG. 5 shows select SEM images of SMCs taken using high magnification.

FIG. 6 shows the percentage confluency of the cells grown on Ch-PPy, chitosan and a normal cell culture dish.

FIG. 7 shows cell growth on Ch-PPy, chitosan and a normal cell culture dish using cell staining.

FIG. 8 shows gelled nodules of Ch-PPy and chitosan injected subcutaneously into rats on day 0.

FIG. 9 shows gelled nodules of Ch-PPy and chitosan injected subcutaneously into rats at 12 weeks.

FIG. 10 shows gelled nodules of Ch-PPy and chitosan injected subcutaneously into rats at 21 weeks.

FIG. 11 shows the biodegradation of gelled nodules of Ch-PPy and chitosan injected subcutaneously into rats.

FIG. 12 shows a 2-point probe was used to measure conductivity of conducting hydrogels.

FIG. 13 shows the results of conductivity measurements for conducting hydrogels.

FIG. 14A shows a custom-fabricated cuvette produced for electrical properties measurements; FIG. 14B show cyclic voltammetry measurements.

FIG. 15 shows EIS measurements of conducting hydrogels.

FIG. 16 shows the biological conductivity of Ch-PPY using cardiomyocyte contraction via full dish coverage (FIG. 18B) and a Ch-PPY spot (FIG. 18C) patterns of Ch-PPy to support cardiomyocyte cell growth.

FIG. 17 shows micrographs of DAPI- and phalloidin-stained neonatal cardiomyocyte dishes.

FIG. 18 shows a schematic diagram and photograph of the two muscle stimulation experiment.

FIG. 19A shows a timeline for the numerous experiments preformed; FIG. 19B shows a visual inspection of the Ch-PPy after injection in the apex and border zone, 1 week after a MI; and FIG. 19C shows the orientation for octapolar catheter recordings.

FIG. 20 shows the results of surface ECGs from an in vivo study.

FIG. 21 shows schematic diagrams of the acute and chronic experimental timelines from an in vivo study testing saline, chitosan and Ch-PPy.

FIG. 22 shows coronary artery ligation of the rat hearts as assessed by echocardiography from an in vivo study testing saline, chitosan and Ch-PPy.

FIG. 23 shows load-dependent cardiac function and LV volumes by pressure-volume (P-V) catheter from an in vivo study testing saline, chitosan and Ch-PPy.

FIG. 24 shows load-independent cardiac function by P-V catheter from an in vivo study testing saline, chitosan and Ch-PPy.

FIG. 25 shows the cardiac function by echocardiography from an in vivo study testing saline, chitosan and Ch-PPy.

DETAILED DESCRIPTION

The present disclosure relates to a biocompatible, electrically conductive biomaterial capable of carrying the electrical potential of a cardiac impulse, as well as treatments using the electrically conductive biomaterial. In particular, the present invention relates to the treatment of MI by introducing a biocompatible, electrically conductive biomaterial to the heart.

As used herein, the term "biocompatible" refers to an article that does not cause toxic or injurious effects on biological systems.

As used herein, the term "biomaterial" refers to a polymer composition, hydrogel or article that is biocompatible. The biomaterial can include an article in different physical forms, such as a hydrogel, membrane, sheet, graft, or mesh. These forms include typical membranes, sheets, grafts, meshes, etc. used in surgery or tissue repair. These articles can include natural products, synthetic products, or combinations thereof. The biomaterial of the present disclosure can be used exclusively to form one of these articles or can be used as a component of one of these articles.

As used herein, the term "hydrogel" refer to a polymeric material, typically a network or matrix of polymer chains, capable of swelling in water or becoming swollen with water. A hydrogel can also be understood to be a material that retains water in an equilibrium state. The network or matrix may or may not be crosslinked.

In one embodiment, the present disclosure relates to a biocompatible biomaterial comprising a conductive polymer and a biocompatible component. Conductive polymers are polymers that are inherently or intrinsically capable of electrical conductivity. In one embodiment, conductive polymers include polymers that exhibit a bulk specific conductance of greater than or equal to about $10^{-5}$ Siemens per centimeter ("S/cm"), or about $10^{-4}$ S/cm, or about $10^{-3}$ S/cm, or about $10^{-2}$ S/cm, or about 1 S/cm, or about 10 S/cm, or about 100 S/cm, or about $10^3$ S/cm. The polymers can also that exhibit a range of bulk specific conductance between any of these values (e.g., between about $10^{-5}$ S/cm and about $10^{-4}$ S/cm, or about $10^{-5}$ S/cm and about 1000 S/cm, or about $10^{-5}$ S/cm and about $10^{-2}$ S/cm, etc.)

The conductive polymer can include polyaniline-based polymers, polypyrrole-based polymers, polyethyleneoxide-based polymers, polythiophene-based polymers, and mixtures or copolymers thereof. In particular, the conductive polymer can include polypyrrole or polyaniline. The conductive polymer can be linear or branched, and have a molecular weight ranging from about 44 to about 18,500 Daltons. In some embodiments, the molecular weight is greater than about 50 Daltons, or about 100 Daltons, or about 200 Daltons, or about 500 Daltons, or about 1,000 Daltons, or about 1,500 Daltons, or about 2,000 Daltons, or about 3,000 Daltons, or about 4,000 Daltons, or about 5,000 Daltons, or about 7,000 Daltons, or about 9,000 Daltons, or about 10,000 Daltons, or about 12,000 Daltons, or about 14,000 Daltons, or about 16,000 Daltons. In other embodiments, the molecular weight is less than about 200 Daltons, or about 500 Daltons, or about 1,000 Daltons, or about 1,500 Daltons, or about 2,000 Daltons, or about 3,000 Daltons, or about 4,000 Daltons, or about 5,000 Daltons, or about 7,000 Daltons, or about 9,000 Daltons, or about 10,000 Daltons, or about 12,000 Daltons, or about 14,000 Daltons, or about 16,000 Daltons, or about 18,500 Daltons. In still other embodiments, the molecular weight can be a range between any of these values (e.g., between about 200 Daltons and about 7,000 Daltons, or between about 50 Daltons and about 10,000 Daltons, etc.).

The biocompatible component can include natural products, synthetic products or combinations thereof. In one embodiment, the biocompatible component can include a natural product, such as a linear or branched polysaccharide, protein or polypeptide. These natural products include chitosan, gelatin, collagen, fibronectin, elastin, alginate, and derivatives and combinations thereof. In another embodiment, the biocompatible component can include a synthetic product, such as a biodegradable synthetic polymer. These synthetic products include polyalkylene oxides, such as polyethylene glycols, and poly(δ-valerolactone), poly(ε-caprolactone), poly(lactide), poly(α-hydroxy acid), poly(glycolide), and derivatives and combinations thereof.

The biocompatible component can have a molecular weight ranging from about 40 to about 200,000 Daltons. In some embodiments, the molecular weight is greater than about 100 Daltons, or about 2,000 Daltons, or about 5,000 Daltons, or about 10,000 Daltons, or about 15,000 Daltons, or about 20,000 Daltons, or about 30,000 Daltons, or about 40,000 Daltons, or about 50,000 Daltons, or about 70,000 Daltons, or about 90,000 Daltons, or about 100,000 Daltons, or about 120,000 Daltons, or about 140,000 Daltons, or about 160,000 Daltons. In other embodiments, the molecular weight is less than about 2,000 Daltons, or about 5,000 Daltons, or about 10,000 Daltons, or about 15,000 Daltons, or about 20,000 Daltons, or about 30,000 Daltons, or about 40,000 Daltons, or about 50,000 Daltons, or about 70,000 Daltons, or about 90,000 Daltons, or about 100,000 Daltons, or about 120,000 Daltons, or about 140,000 Daltons, or about 160,000 Daltons, or about 180,000 Daltons, or about 200,000 Daltons. In still other embodiments, the molecular weight can be a range between any of these values (e.g., between about 2,000 Daltons and about 70,000 Daltons, or between about 20,000 Daltons and about 100,000 Daltons, etc.).

In one embodiment, the biocompatible component is chitosan having a molecular weight between about 10,000 and about 200,000 Daltons. In another embodiment, the biocompatible component is gelatin having a molecular weight between about 10,000 and about 300,000 Daltons.

The conductive polymer and the biocompatible component can be combined to form an electrically conductive biomaterial. The molar ratio of the conductive polymer and biocompatible component in the biomaterial can range from 1000:1 to 1:1000, respectively. In some embodiments, the molar ratio of the conductive polymer and biocompatible component can be greater than about 1:3, or about 1:2, or about 1:1, or about 2:1, or about 3:1, or about 5:1, or about 10:1, or about 25:1, or about 50:1, or about 100:1, or about 150:1, or about 200:1, or about 250:1, or about 300:1 or about 350:1 or about 400:1, or about 500:1. In other embodiments, the molar ratio of the conductive polymer and biocompatible component can be less than about 1:2, or about 1:1, or about 2:1, or about 3:1, or about 5:1, or about 10:1, or about 25:1, or about 50:1, or about 100:1, or about 150:1, or about 200:1, or about 250:1, or about 300:1 or about 350:1 or about 400:1, or about 500:1, or about 1000:1.

In still other embodiments, the molar ratio of the conductive polymer and biocompatible component can be a range between any of these values (e.g., between 1:1 to 1:350, or between 1:3 to 1:150, or between 3:1 and 300:1, etc.). In one embodiment, the ratio is 2.1:1 to 1000:1.

In some embodiments, the molecular weight of the biomaterial can range from about 1,000 to about 1,000,000 Daltons. In some embodiments, the molecular weight of the biomaterial is greater than about 1,000 Daltons, or about 2,000 Daltons, or about 5,000 Daltons, or about 10,000 Daltons, or about 20,000 Daltons, or about 50,000 Daltons, or about 100,000 Daltons, or about 150,000 Daltons, or about 200,000 Daltons, or about 300,000 Daltons, or about 400,000 Daltons, or about 500,000 Daltons, or about 600,000 Daltons, or about 700,000 Daltons, or about 800,000 Daltons. In other embodiments, the molecular weight of the biomaterial is less than about 2,000 Daltons, or about 5,000 Daltons, or about 10,000 Daltons, or about 20,000 Daltons, or about 50,000 Daltons, or about 100,000 Daltons, or about 150,000 Daltons, or about 200,000 Daltons, or about 300,000 Daltons, or about 400,000 Daltons, or about 500,000 Daltons, or about 600,000 Daltons, or about 700,000 Daltons, or about 800,000 Daltons, or about 1,000,000 Daltons. In still other embodiments, the molecular weight of the biomaterial can be a range between any of these values (e.g., between about 5,000 Daltons and about 800,000 Daltons, or between about 20,000 Daltons and about 100,000 Daltons, etc.).

In one embodiment, the biomaterial has a molecular weight about 350,000 Daltons (i.e., comprising chitosan having a molecular weight of about 50,000 Daltons and gelatin having a molecular weight of about 300,000 Daltons).

The conductivity of the biomaterial is primarily attributed to the presence of the conducting polymer. In one embodiment, the conductivity of the biomaterial is greater than or equal to about $10^{-5}$ S/cm. In some embodiments, the conductivity of the biomaterial is greater than or equal to about $10^{-4}$ S/cm, or about $10^{-3}$ S/cm, or about $10^{-2}$ S/cm, or about 1 S/cm, or about 10 S/cm. In other embodiments, the conductivity of the biomaterial is less than or equal to about $10^{-5}$ S/cm, or about $10^{-4}$ S/cm, or about $10^{-3}$ S/cm, or about $10^{-2}$ S/cm, or about 1 S/cm, or about 10 S/cm. In one embodiment, the conducting biomaterial, polymer and/or the hydrogel is able to carry the electrical potential of a cardiac impulse at about 100 mV. The repolarization voltage of tissue is about 40 mV. In particular, these materials are able to carry the electrical potential of a cardiac impulse about 40 mV or greater. In particular embodiments, the materials are able to carry the electrical potential of a cardiac impulse of about 10 to about 250 mV, or about 20 to about 200 mV, or about 50 to about 150 mV, or about 75 to about 100 mV, or any combination of these values (e.g., about 50 to about 100 mV, etc.).

Similarly, in some embodiments the conductive biomaterials can have resistivities (or volume resistivities) greater than about 0.06 ohm centimeter ($\Omega$cm), or about 0.1 $\Omega$cm, or about 0.6 $\Omega$cm, or about 1 $\Omega$cm, or about 10 $\Omega$cm, or about 100 $\Omega$cm, or about 1,000 $\Omega$cm, or about $10^4$ $\Omega$cm, or about $10^5$ $\Omega$cm, or about $2\times10^5$ $\Omega$cm. In other embodiments the conductive biomaterials can have resistivities less than about 0.1 $\Omega$cm, or about 0.6 $\Omega$cm, or about 1 $\Omega$cm, or about 10 $\Omega$cm, or about 100 $\Omega$cm, or about 1,000 $\Omega$cm, or about $10^4$ $\Omega$cm, or about $10^5$ $\Omega$cm, or about $2\times10^5$ $\Omega$cm. In still other embodiments, the conductive biomaterials can have resistivities in a range between any of these values (e.g., between about 0.6 $\Omega$cm and about 100 $\Omega$cm, or between about 0.0625 and about $2\times10^5$ $\Omega$cm, or between 0.6 to about $2\times10^3$ $\Omega$cm, etc.). Resistivity (or volume resistivity) is defined as equal to: Resistance (n)=distance/Area (cm$^2$)× Thickness (cm). In one embodiment, the resistivity is between about 50 and about 20,000 $\Omega$cm.

The hydrogel can also contain a crosslinking agent used to crosslink the present hydrogels and to assist in hydrogel formation. The crosslinking agent can be a known crosslinking agent and contain electrophilic groups, nucleophilic groups, or both. The crosslinking agent can be a natural product or a synthetic product. Examples of multi-functional crosslinking agents which may be used include, for example, gluteraldehyde, methylene-bis-acrylamide, diethylene glycol diacrylate, ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, and other polyacrylate and polymethacrylate esters. In one embodiment, the crosslinking agent is genipin or tannic acid. As used herein, the term "genipin" is meant a compound recognized as genipin as a chemical compound or an equivalent of genipin as a chemical compound by a person of ordinary skill in the art. The term "genipin" is intended to cover derivatives, analog, stereoisomers and mixtures thereof. The genipin compound can be derived from natural sources or synthetically made.

The amount of crosslinking agent can be within the range of about 0.001 to about 10% by weight. In particular, the amount can be within the range of about 0.005 to about 5% by weight, or about 0.01 and about 3%, or any combination thereof. The crosslinker can be added to the material just prior to introduction (e.g., 1-10 minutes prior to introduction). In some embodiments, it takes 1-10 minutes for the biomaterial to gel. During the gelling time, the biomaterial can be introduced.

In another embodiment, the present disclosure relates to a method of treating a heart condition, the method comprising introducing a biocompatible biomaterial to the heart, wherein the biomaterial includes a conductive polymer and a biocompatible component. The heart condition can include myocardial infarction, heart failure, atrioventricular block, arrhythmia and a conduction abnormality.

Without wishing to be bound, it is believed the electrically conductive biomaterial can promote beneficial remodeling of the border zone area following an infarct (i.e., a method of remodeling). The biomaterials can prevent fibrotic tissue expansion, heart chamber dialation and induce blood vessel formation (i.e., a method of preventing expansion and/or dialation, or inducing formation). All these changes can benefit heart function and prevent heart failure. The conductive biomaterial can also improve conduction velocities across fibrotic tissues by lowering the threshold for cardiac action potential propagation (i.e., a method of improving velocities). For example, the conductive material can be introduced to fibrotic tissue of the injured region. The material will decrease resistance of the fibrotic tissue and increase current through the tissue. The electrically conductive biomaterial can restore or improve electrical impulse propagation across the scar region of the myocardium and resolve "passive" barriers to atrioventricular electrical conduction (i.e., a method of restoring or improving propagation). Finally, the conductive biomaterial (e.g., hydrogel) can also improve the performance of implantable pacemaker devices and ultimately, may serve as an alternative to cardiac ablation for the treatment of some cardiac arrhythmias (i.e., a method of improving the performance of a pacemaker).

The conductive biomaterial can change the fibrotic resistance, which will enhance performance of the stimulator function.

The biocompatible biomaterial (e.g., hydrogel) can be introduced by known method of treating biological tissue and organs with a hydrogel and similar materials. In one embodiment, material can be injected into or onto the heart. The conductive biomaterials can also be formed in sheet, or other articles, which can be used on top of the injured tissue. For example, the conductive biomaterial can be generated as graft. The excess fibrotic tissue can be removed and conductive biomaterial graft can be put and repair the defect area.

In one embodiment, the amount of biomaterial (e.g., hydrogel) introduced to the tissue or organ can depend on a number of factors, such as the composition of the biomaterial, the location and the condition of the tissue or organ, the size of the tissue or organ and/or the size of the damaged or area to be treated. In one embodiment, the volume of biomaterial can range from about 1 µl to about 10 mL, or about 2 µl to about 5 mL, or about 5 µl to about 3 mL, or about 10 µl to about 2 mL, or about 50 µl to about 1 mL, or about .or about 100 µl to about 500 µl, or any combination of these values (e.g., about 1 mL to about 2 mL, etc.)

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

The following examples are based on the use of both mouse and rat models of early and late phase MI. An AV block model with in vivo and ex-vivo rat heart preparations has also been developed. These examples are also based on and can be used with an array of injectable biomaterial hydrogels that can act as carriers for cells and cytokines, and help to retain cells, enhance their survival, and support the timed release of cytokines and growth factors. These injectable biomaterials are easy to manipulate, and can be chemically modified with a variety of molecules including peptide fragments, proteins and antibodies. They are also biocompatible, and their degradation products are safe for use in vivo.

The examples presented here and in the Figures demonstrate the intrinsic biocompatible, and conductive properties of the hydrogels of the present disclosure, e.g. polypyrrole (PPy)-chitosan hydrogels.

Example 1—Synthesis of a PPy-Chitosan Hydrogel

A biocompatible and conductive biomaterial was prepared by grafting pyrrole onto chitosan. FIGS. 1 and 2A illustrate the grafting procedure that has been established. In general, chitosan is dissolved in water and acetic acid. Thereafter, pyrrole monomer is added to the chitosan solution in the presence of iron (III) chloride. The Pyrrole polymerizes into polypyrrole and forms side chains on the chitosan backbone. At end of the reaction, the samples are dialyzed to filter out unbound pyrrole monomers.

Chitosan, a linear polysaccharide, was selected in the form of a hydrogel with suitable mechanical and cell-compatible properties for in vitro and in vivo studies. Pyrrole was crosslinked to chitosan using ferric chloride as a catalyst to produce a copolymer solution. Three different concentrations were produced with the highest being 284 mg Pyrrole/gram chitosan. FIG. 2B illustrates the homogeneous nature of PPy-chitosan hydrogel.

Chitosan-Polypyrrole (Ch-PPy or PPy-Ch) Preparation: 0.200 g of Chitosan is dissolved in 10 mL of water containing 100 µL of (glacial) Acetic Acid. The solution is mixed with a stir bar on a stirring plate. 60 µL of Pyrrole is added to the Chitosan solution to provide a Ch-PPy concentration of 284 mg Pyrrole/g Chitosan (Sample A). For a Ch-PPy concentration of 28.4 mg Pyrrole/g Chitosan (Sample B) or a Ch-PPy concentration of 2.84 mg Pyrrole/g Chitosan (Sample C), add 6 µL Py to 10 mL Ch or 0.6 µL Py to 10 mL of Ch respectively. The solution is then mixed well. 0.180 g of $FeCl_3$ for sample A (0.0180 g of $FeCl_3$ for sample B or 0.0018 g of $FeCl_3$ for Sample C) is dissolved in 0.5 mL of dd water. The $FeCl_3$ solution is dropped into the Ch-PPy solution while stirring. The solution is then stirred well to allow the Pyrrole monomers to polymerize into Polypyrrole which form side chains on the Chitosan backbone. The molecular weight range of different Ch-PPy materials made is between about 50,000 and about 200,000 Daltons.

The chitosan-polypyrrole forms a gel in the presence of a cross-linking agent, such as gluteraldehyde. Gelation was achieved by neutralizing the pH and using gluteraldehyde as the crosslinker. (See FIG. 2C). In some instances, prior to crosslinking (or fully crosslinking) the PPy-chitosan can be molded into desired shapes. These shapes can be used as injectable material before full crosslinking occurs. Three different samples of PPy-Ch were tested and shown to form gels in the presence of gluteraldehyde solutions. FIG. 3 shows the results of the gelation test.

Example 2—Cell Attachment and Proliferation

A biocompatibility study was performed to evaluate whether mammalian cells can grow on the Ch-PPy gel. If the biomaterial is biocompatible and non-toxic, it will support the growth of mammalian cells. Cell culture dishes were coated with CH-PPy gel. Cultured smooth muscle cells (SMCs) were seeded onto the biomaterial-coated dishes and cultured for 1, 3, and 7 days. On each day, the cultured cells were imaged by microscopy. FIG. 4 shows the images taken at these time points using low magnification. FIG. 5 shows these images at a higher magnification. The area covered with cells was calculated. FIG. 6 shows the percentage confluency of the cells grown on Ch-PPy, chitosan (an established biomaterial) and a normal cell culture dish. FIG. 7 shows cell growth on these dishes using cell staining.

Example 3—In Vivo Degradation Assay

An in-vivo study was performed to test the in-vivo degradation of the Ch-PPy hydrogels. Ch-PPy (100 µL) or chitosan alone (100 µL) solutions were injected subcutaneously into rats. Injected Ch-PPy and chitosan gelled immediately and formed nodules subcutaneously. The diameters of the resultant nodules were measured immediately (day 0) and 2, 4, 8 and 21 weeks post-injection. FIG. 8 shows the gelled nodules on day 0. The nodule sizes are similar between the groups at day 0. The nodules can still be observed at 12 weeks (See FIG. 9). At 12 weeks, the chitosan degraded (dissolved) faster than Ch-PPy (~39% faster). At 21 weeks, the nodule sizes decreased significantly (See FIG. 10). The Ch-PPy nodule size decreased more slowly compared with chitosan. The Ch-PPy has retained 70% of its original size while chitosan has only retained 39% of its original size. The biodegradation is summarized in the graph shown in FIG. 11. The chitosan degraded significantly faster than Ch-PPy. At 21 weeks after injection, the chitosan has lost 61% of its original size while Ch-PPy only lost 30% of its original size.

The conducting hydrogels of the present disclosure are biodegradable. The degradation rate can be adjusted depending the composition of components. In one embodiment, the conducting hydrogel biodegrades between about 1 week and about 12 weeks. In particular, the conducting hydro gel biodegrades between about 2 weeks and about 10 weeks, or between about 3 weeks and about 9 weeks, or about 4 weeks and about 8 weeks, or about 5 weeks and about 7 weeks, or any combination thereof (e.g., between about 8 and about 12 weeks).

Example 4—Conductivity

The electrophysiological function of the conductive biomaterial was investigated. Ch-PPY conductivity was quantified in gel form. A 2-point probe was used to measure conductivity as shown in FIG. 12. A voltage difference was applied between two probes placed about 7 mm apart, and into a 4 mm thick biomaterial sample, giving a current output measured in amperes. The current was plotted against the voltage range to compare of conductivity.

Three concentrations of the Ch-PPY biomaterial were tested for their conductivity. Gelatin (an extracellular material), and chitosan were used as controls. The results are presented in FIG. 13. Gelatin has very low conductive activity. Chitosan is about 7 times more conductive in comparison. The highest concentration of Ch-PPY material is more conductive than the lowest concentration of Ch-PPY, as well as the chitosan control. Furthermore, the lowest concentration Ch-PPY is no more conductive than chitosan, suggesting that there may be a threshold PPY concentration that makes the biomaterial conductive.

In some embodiments, the concentration of Ch-PPy is greater than about 2.84 mg pyrol/gram chitosan. In other embodiments, the concentration of Ch-PPy is greater than or equal to about 250 mg pyrol/gram chitosan. More particularly, the concentration of Ch-PPy is greater than or equal to about 300 mg pyrol/gram chitosan, or about 400 mg pyrol/gram chitosan, or about 500 mg pyrol/gram chitosan, or about 1000 mg pyrol/gram chitosan, or about 2000 mg pyrol/gram chitosan.

The PPy-chitosan electrical properties were further characterized using a custom-fabricated 1 cubic cm cuvette with copper sides for electrochemical impedance spectroscopy (EIS) and cyclic voltammetry recordings. FIG. 14A shows the custom-fabricated cuvette produced for each measurement. FIG. 14B shows voltammograms for four groups tested (chitosan control, 0.23% PPy-chitosan (2.84 mg pyrol/gram chitosan), 2.3% PPy-chitosan (28.4 mg/g), and 23% PPy-chitosan (284 mg/g). These tests demonstrate that PPy-chitosan possesses hysteresis properties (e.g., non-linear conductive properties). EIS measurements are shown in FIG. 15C. These measurements reveal that as the PPy composition is increased, impedance decreases, particularly at the lower frequency ranges. Conductivity was directly assessed from thinly-coated polystyrene dishes using a four-point probe method (See FIG. 15D). Two sets of working electrodes were used to measure the resistance of the material. Conductivity was derived from these results.

Example 5—Biological Function of Conductive Biomaterial In Vitro

The biological conductivity of Ch-PPY was tested using cardiomyocyte contraction. Neonatal rat cardiomyocytes were isolated and seeded onto sterile Ch-PPY and blank control dishes. The cells were grown for 7 days to achieve confluent beating monolayers. Two different patterns of Ch-PPY were used to support cardiomyocyte cell growth: full dish coverage (FIG. 16B) and a Ch-PPY spot (FIG. 16C). For the spot patterns, a concentric circle of Ch-PPY measuring approximately half the diameter of the dish itself was placed in the middle of the dish, and the rest of the dish left blank. The purpose of the pattern was to serve as an important control. With coated and non-coated areas are in the same dish, receiving the same cells, same media, same staining, and same incubation, a more effective comparison can be made between cells grown on Ch-PPY and those in normal culture conditions.

Fully coated Ch-PPY dishes showed far different cardiomyocyte contractility and Ch-PPY conduction. Cardiac impulses were more instantaneous and synchronized across the dish, rather than following a path or orientation. It appeared as if all cells were beating at the same time, with no delay in transferring action potentials. This suggests that the Ch-PPY is functional and can electrically connect the entire monolayer. Micrographs of DAPI- and phalloidin-stained neonatal cardiomyocyte dishes are shown in FIG. 17.

Example 6—Two Muscle Stimulation Experiment

Another proof of concept experiment for the application of the conductive polymer was performed with a two muscle stimulation experiment. FIGS. 18(A and B) show a schematic diagram and photograph of the two muscle stimulation experiment. A thick layer of control gelatin or 23% PPy-gelatin was coated onto the surface of a 60-mm dish. Two similar sized skeletal muscles were removed from a rat hindlimb and immediately placed on posts in the dish. The muscles were trimmed so that they were the same weight. One muscle was stimulated directly using a programmable stimulator and tested at several voltages. The action potentials and voltage amplitudes produced by the other skeletal muscle were recorded. PPY-gelatin facilitated the production of larger action potentials versus the control. As shown in FIG. 18C, the conducting hydrogels are lowering the resistivity surrounding the two skeletal muscle tissue (*$p<0.01$, # $p<0.05$, n=5 experiments/group).

Example 7—Assessment of Conductive Biomaterial in In Vivo Model

A first series of in vivo studies were performed to demonstrate an improvement in heart function. All surgical procedures were approved by the Animal Care Committee of the University Health Network (Toronto, Canada). In this study, the echocardiographic function of different groups of animals (n=4 or 6 animals) at multiple time points leading up to 8 weeks was studied. PV-loop analysis is used to examine load-dependent and load-independent changes in cardiac function, and further optical mapping studies will be carried out wherever possible.

As shown in FIG. 19A, a timeline depicts the numerous experiments preformed on animals at various time points throughout the study. Three groups were tested with saline, chitosan only and Ch-PPy, respectively. Endpoints included recording of direct myocardial ECGs using an octapolar catheter; ex vivo Langendorff perfusion of rat hearts to facilitate optical mapping using the voltage sensitive dye di-4 anneps; and fixation and processing of tissues for histology at a later time. FIG. 19B is a visual inspection of the Ch-PPy after injection in the apex and border zone, 1 week after a MI. FIG. 19C shows the orientation for octapolar catheter recordings.

Surface ECGs were recorded using three leads throughout the 18-week experiment. FIG. 20 shows the results. In FIG. 20, time points shown are baseline (−2 weeks); 1 week post MI (−1 week); and 8 and 16 weeks post injection. As shown in FIG. 20A, there was a difference in heart rate between the three groups. As shown in FIG. 20B, there was significant reduction in QRS-interval for the PPy-Ch group vs. control at both 8 and 16 weeks post injection. This suggest enhanced left ventricle conduction. As shown in FIGS. 20C and 20D, there was no difference between the groups in terms of repolarization kinetics as evidenced by QT-interval and QTc analysis (*$p<0.05$; $p<0.01$; n=4 or 6 animals per group/time point).

Optical mapping data provides evidence of changes in conduction velocity in the left ventricular free wall, particularly in the border zone area. Analysis of the direct epicardial electrophysiological recordings obtained at the final time point support these findings. Finally, histological evaluation of myocardial tissue at the end of the study was used to quantify the scar size/area, as well as retention or degradation of the injected biomaterials. The expression of connexin proteins in the border zone area was also examined, and indicated a change in the conduction velocity observed in the optical mapping experiments.

The improvement observed with the conducting biomaterial of the present disclosure appears likely due to enhanced cardiac conduction and beneficial conductive remodeling. This is evidenced, in part, by enhancement in cardiac function (EF %, FAC % and FS %) and by shortening of the QRS-interval. This important electrophysiological parameter suggests that cardiac depolarization, particularly through the left ventricle, occurs more quickly in Ch-PPy injected hearts versus chitosan and saline-injected controls. By lowering the threshold required for electrical propagation to passively travel through the border zone and scar area in this long-term MI model, over time, global cardiac function is enhanced.

Example 8—Biological Function of Conductive Biomaterial In Vivo (1) Implantation of Conductive Biomaterial to Benefit Cardiac Function in an Acute and Chronic Myocardial Infarction (MI) Model Again, all surgical procedures were approved by the Animal Care Committee of the University Health Network (Toronto, Canada). Female Sprague-Dawley rats (225-250 g) were anesthetized, intubated and perfused with 2% isoflurane mixed with oxygen. The chest was opened by a left lateral therorectomy, and a single stitch of 7-0 prolene suture was introduced around the left anterior descending coronary artery and tightened. The chest was then closed and the animal was allowed to recover for 1 week (acute) or 2 months (chronic). These acute and chronic infarct models have previously been shown to create infarct sizes of approximately 35% of the left ventricle (LV). Schematic diagrams of the acute and chronic experimental timelines are shown in FIG. 21.

(2) Biomaterial Injection

One week (acute) or 2 months (chronic) after MI, rats were randomized into chitosan only, Ch-PPy, or phosphate-buffered saline (PBS) control groups (n=6-11/group). The animals were anesthetized, intubated and the chest opened by a left lateral therorectomy. A total volume of 100 uL in each group was injected into the peri-infarcted LV region of each heart, using a 500 uL tuberculin syringe and a 28-gauge needle. The chest was then closed and the animal allowed to recover for 8 weeks (acute) or 3 months (chronic). After these time periods, the rats were euthanized with an isoflurane overdose (5%).

(3) Cardiac Functional Measurements

Function was evaluated using echocardiography immediately before MI, immediately before biomaterial or saline injection, and at 2, 4, and 8 weeks (acute) or 1 and 3 months (chronic) after injection. Cardiac function was also assessed at the end of the study with a pressure-volume catheter. All data are expressed as mean+/−standard deviation. Student's t-test and one- or two-way analysis of variance (ANOVA) followed by Bonferroni's post hoc test were used for parameter estimation and hypothesis testing, with $p<0.05$ being considered statistically significant.

Cardiac Function—Echocardiography for Acute Study

Coronary artery ligation of the rat hearts resulted in significant LV dilatation and progressive ventricular dysfunction, as assessed by echocardiography (See FIG. 22). All echocardiographic parameters were virtually indistinguishable among the animals at the time of biomaterial injection (Week 0; See FIGS. 22A-D) due to the pre-selection of animals with similar infarct sizes. Four weeks following injection, fractional shortening and fractional area change in the saline group had decreased more than in the chitosan and Ch-PPY groups (See FIGS. 22A-B). At 8 weeks, the protective effect of the Ch-PPY injection was reflected in the significant preservation of fractional shortening and fractional area change compared with the saline and chitosan groups (See FIGS. 22A-B). The left ventricular internal systolic dimension (LVIDs) and end systolic area (LVESA) in the saline group increased by week 2 and continued this trend to week 8 (See FIGS. 22C-D). In contrast, the structural stabilization effect of chitosan and Ch-PPY resulted in smaller systolic dimensions and areas. At 8 weeks after injection, the Ch-PPY group demonstrated the greatest protective effect, possibly due to enhanced electrical conductivity ($p<0.05$ vs. chitosan group). LVIDs and LVESA in the chitosan group were significantly smaller compared with saline group, and Ch-PPy group had the smallest dimension and area.

Also observed from FIG. 22 is fractional shortening (FS) and fractional area change (FAC) decreased dramatically in all groups from ligation (Week −1) to biomaterial injection (Week 0) and continued to decrease in the saline and biomaterial groups. Left ventricular internal systolic dimension (LVIDs) and end systolic area (LVESA) increased dramatically in all groups from ligation (Week−1) to polymer injection (Week 0), and this trend continued in the saline and chitosan groups.

Cardiac Function—Pressure-Volume Catheter for Acute Study

Ventricular volumes and cardiac function were evaluated under load-dependent (FIG. 23) and load-independent (FIG. 24) conditions. Compared with saline, chitosan improved ejection fraction (EF), Dp/dt max, Dp/dt min, and Tau (load-dependent indices), as well as end-systolic elastance (ESPVR) and preload recruitable stroke work (PRSW) (load-independent indices). Ch-PPY further improved EF, Dp/dt max, Dp/dt min, Tau, ESPVR, and PRSW ($p<0.01$ vs. saline, # $p<0.05$ vs. chitosan). End-systolic volume was smallest in the Ch-PPY group, followed by the chitosan group. All polymer treatments reduced end-systolic volumes relative to saline ($p<0.01$ for all groups).

As shown in FIG. 23, left ventricular (LV) P-V relationships were measured at 8 weeks after post-MI injection of saline, chitosan and Ch-PPy (A-D). Compared with the saline group, load-dependent measures ejection fraction (A), Dp/dt max (B), Dp/dt min (C), and Tau_W (D) were significantly improved, and LV end systolic volume (E) was smaller (**$p<0.01$) in the chitosan compared with saline group. Importantly, Ch-PPy demonstrated the greatest (# $p<0.05$ vs. chitosan) protective effects for all measures.

As shown in FIG. 24(A-C), representative series of P-V loops obtained during vena cava occlusion at 8 weeks after post-MI injection of saline (A), chitosan (B), or Ch-PPy (C). In FIG. 24(D, E), load-independent measures of end systolic pressure-volume relationship (ESPVR, D) and preload recruitable stroke work (PRSW, E) were significantly improved ($p<0.01$) in the chitosan compared with saline group. Importantly, Ch-PPy demonstrated the greatest ($p<0.05$ and 0.01 vs. chitosan respectively) protective effect.

Cardiac Function—Echocardiography for Chronic Study

Coronary artery ligation of the rat hearts resulted in significant LV dilatation and progressive ventricular dysfunction, as assessed by echocardiography. (See FIG. 25). All echocardiographic parameters were virtually indistinguishable among the animals at the time of biomaterial injection (2 months after MI; See FIG. 25A-D) due to the pre-selection of animals with similar infarct sizes. At 3 months after biomaterial injection (5 months after MI), the protective effect of the Ch-PPY injection was reflected in the significant preservation of fractional shortening compared with the saline and chitosan groups (See FIG. 25A). The left ventricular internal systolic and diastolic dimensions (LVIDs and LVIDd) in the saline and chitosan groups increased by month 1 and continued this trend to 3 months after biomaterial injection (See FIGS. 25B-C). In contrast, the effect of Ch-PPY resulted in smaller systolic and diastolic dimensions and demonstrated the greater protective effect compared with saline and chitosan 3 months after injection, possibly due to enhanced electrical conductivity ($p<0.05$ vs. chitosan and $p<0.01$ vs. saline). Additionally, serial Doppler echocardiography tests suggest that diastolic properties were improved in Ch-PPY treated rats. During a 3-month follow-up, saline and chitosan-treated animals developed a restrictive LV filling pattern presented by increased E/A ratio (See FIG. 25D, $p<0.01$). In contrast, diastolic function improved in Ch-PPY treated hearts at 1 and 3 months after biomaterial injection (See FIG. 25D, $p<0.01$).

As shown in FIG. 25(A), fractional shortening (FS) decreased dramatically in all groups from ligation (Month 0) to biomaterial injection (Month 2) and continued to decrease in the saline and chitosan groups. As shown in FIG. 25(B), left ventricular internal systolic dimension (LVIDs) increased dramatically in all groups from ligation (Month 0) to biomaterial injection (Month 2) and this trend continued in the saline and chitosan groups. As shown in FIG. 25(C), left ventricular internal diastolic dimension (LVIDd) increased dramatically in all groups from ligation (Month 0) to biomaterial injection (Month 2) and this trend continued in all groups. However, at 3 month after biomaterial injection, LVIDd in the Ch-PPy group was significantly smaller compared with saline group ($p<0.01$). As shown in FIG. 25(D), serial Doppler echocardiography tests suggest that diastolic properties were improved in Ch-PPy treated rats at 1 and 3 month after injection.

While this disclosure has been particularly shown and described with reference to example embodiments thereof, it will be understood by those skilled in the art that various changes in form and details may be made therein without departing from the scope of the invention encompassed by the appended claims.

I claim:

1. A biocompatible material for treating a heart comprising
   a conductive polymer comprising a polypyrrole-based polymer; and
   a biocompatible component comprising chitosan,
   wherein the biocompatible material is prepared by:
   mixing the conductive polymer and the biocompatible component in solution to form a copolymer solution;
   neutralizing the pH of the copolymer solution; and
   allowing the conductive polymer and the biocompatible component to crosslink to form a hydrogel in the presence of a cross-linking agent;
   and wherein the biocompatible material is biocompatible with cardiac tissue.

2. The biocompatible material of claim 1, wherein the conducting polymer has a bulk specific conductance of greater than or equal to about $10^{-5}$ Siemens per centimeter.

3. The biocompatible material of claim 1, wherein the biocompatible material is produced by further molding the hydrogel into a desired shape.

4. The biocompatible material of claim 1 wherein the crosslinking agent is gluteraldehyde, methylene-bis-acrylamide, diethylene glycol diacrylate, ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, polyacrylate esters, polymethacrylate esters, genipin, or tannic acid.

5. The biocompatible material of claim 4 wherein the crosslinking agent is gluteraldehyde.

6. A method of treating a heart condition, the method comprising
   introducing the biocompatible material of claim 1 to the heart, wherein the material includes a conductive polymer and a biocompatible component.

7. The method of claim 6, wherein the heart condition is myocardial infarction, heart failure, atrioventricular block, arrhythmia or a conduction abnormality.

8. The method of claim 6, wherein the conducting polymer has a bulk specific conductance of greater than or equal to about $10^{-5}$ Siemens per centimeter.

* * * * *